(12) United States Patent
Yoshida

(10) Patent No.: US 6,795,573 B2
(45) Date of Patent: Sep. 21, 2004

(54) INSPECTION METHOD AND APPARATUS

(75) Inventor: Kouji Yoshida, Tokyo (JP)

(73) Assignee: Nikon Corporation, Tokyo (JP)

( * ) Notice: Subject to any disclaimer, the term of this patent is extended or adjusted under 35 U.S.C. 154(b) by 696 days.

(21) Appl. No.: 09/769,303

(22) Filed: Jan. 26, 2001

(65) Prior Publication Data
US 2001/0012394 A1 Aug. 9, 2001

(30) Foreign Application Priority Data

Jan. 27, 2000 (JP) .......................................... 2000-018182
Jan. 27, 2000 (JP) .......................................... 2000-018188

(51) Int. Cl.[7] ................................................. G06K 9/00
(52) U.S. Cl. ............................. 382/149; 382/146; 382/147
(58) Field of Search ............................. 382/141, 143–151; 348/86, 87, 125, 126; 700/95, 96; 438/16; 356/237.1, 237.2, 237.4, 237.5

(56) References Cited

U.S. PATENT DOCUMENTS 5,204,910 A * 4/1993 Lebeau ........................ 382/152
5,943,437 A * 8/1999 Sumie et al. ................ 382/149
6,553,137 B1 * 4/2003 Tomimatu .................... 382/148

FOREIGN PATENT DOCUMENTS

JP        11-304718        11/1999

* cited by examiner

Primary Examiner—Vikkram Bali
(74) Attorney, Agent, or Firm—Oblon, Spivak, McClelland, Maier & Neustadt, P.C.

(57) ABSTRACT

A statistical processing unit compares the gray levels at identical positions in raw and reference images using a raw image having three or more gray levels obtained by sensing an object by an image pick-up unit. As the reference image, a predetermined designed image or at least one shift image obtained by shifting the raw image by an integer multiple of the repetition period in the repetition direction of a specific pattern is used. The statistical processing unit statistically analyzes the occurrence state of the difference between the raw and reference images, thus accurately obtaining the formation state of repetitive patterns on the object.

35 Claims, 19 Drawing Sheets

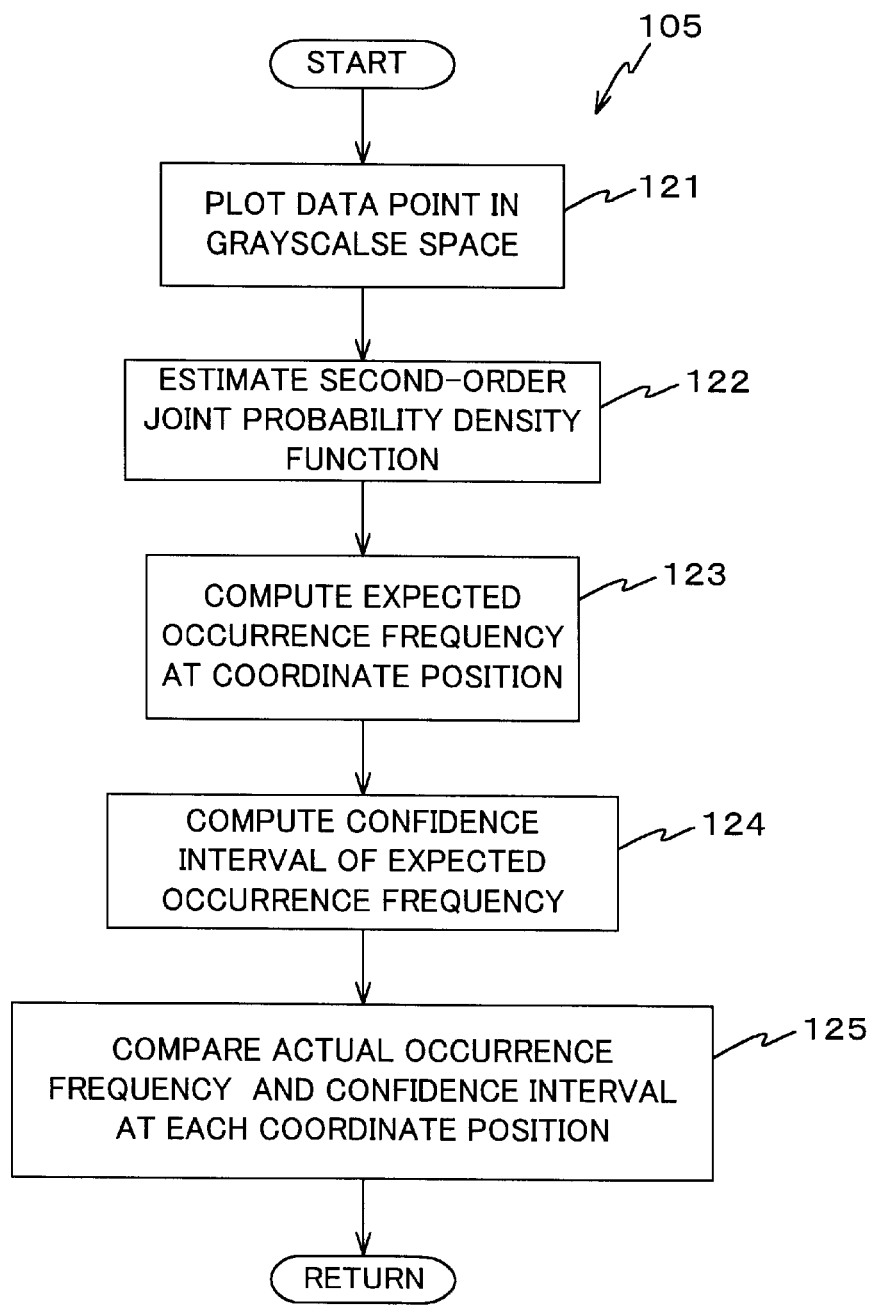

INSPECTION METHOD AND APPARATUS

BACKGROUND OF THE INVENTION

1. Field of the Invention

The present invention relates to an inspection method and apparatus and, more particularly, to an inspection method and apparatus for inspecting the formation state of a pattern on an object on which repetitive patterns are formed.

2. Description of the Related Art

In the manufacturing processes of semiconductor devices, liquid crystal display devices, and the like, circuit patterns and the like are formed sequentially on a substrate such as a wafer or a glass plate (to be referred to as a "substrate" or "wafer" hereinafter as needed). And an inspection apparatus for checking the formation state of the patterns is used in a predetermined step in the manufacturing process. As such inspection apparatus, an optical image inspection apparatus using light such as a laser beam, and an electron image inspection apparatus such as a scanning microscope using an electron beam have been put into practical use.

On the substrate of the semiconductor device or the like, identical patterns are periodically formed in each unit of so-called shot area. In a memory device or a liquid crystal display device, an identical pattern is periodically formed even in a single shot area.

As a technique for detecting any foreign matter or pattern defects (to be referred to as "pattern defects" hereinafter) on the substrate surface on which periodic repetitive patterns must be formed, a technique for comparing a raw image which is an optical or electron image obtained by the inspection apparatus and a shift image obtained by shifting the raw image by the repetition pitch (to be referred to as a "neighbor comparison method" hereinafter) has been proposed. And the neighbor comparison method is prevalently used as the inspection method of the formation state of periodic patterns. In such neighbor comparison method, a binary image having the number of gray level=2 is conventionally used, but a gray image with 3 or more gray level or continuous gray level (to be referred to as a "multi-gray level image" hereinafter) is often used today. In the neighbor comparison method, pattern defects or the like are estimated to be present at an image position where the difference value as a comparison result becomes equal to or larger than a predetermined value (threshold value).

As described above, in the conventional neighbor comparison method, actually formed patterns are compared. The actually formed patterns inevitably include errors from an expectation pattern which is to be originally formed upon pattern formation. For this reason, even when the difference between the signal levels (gray levels) of the raw and shift images at their identical positions is small, the differences between each signal level of the two images and the signal level (to be referred to as an "expectation level" hereinafter) of the expectation pattern are not always small. Even when the difference between the signal levels (gray levels) of the raw and shift images at their identical positions is large, the differences between each signal level of the two images and the expectation level are not always large.

That is, according to the conventional neighbor comparison method, even when the signal level at each image position has a large difference from the expectation level, pattern defects or the like are often not estimated to be present. In this case, even when pattern defects are present, they cannot be recognized. On the other hand, even when the signal level at each image position is not largely different from the expectation level, pattern defects are estimated to be present. In this case, even when no pattern defects are present, a false detection of the pattern defects occurs.

As described above, a multi-gray level image is prevalently used, and the difference between the signal levels at each image position is used, but binary information indicating whether or not the "difference" value is larger than a threshold value is merely obtained. That is, only basically the same information as that obtained using a binary image is obtained. For this reason, although a multi-gray level image is used, information included in the "difference" value is not always fully utilized. That is, a technique for accurately inspecting the substrate surface, on which periodic repetitive patterns are to be formed, for pattern defects by fully utilizing information obtained by a multi-gray level image is demanded.

SUMMARY OF THE INVENTION

The present invention has been made in consideration of the above situation, and has as its object to provide an inspection method and apparatus which can accurately inspect the formation state of periodic repetitive patterns on an object.

According to the first aspect of the present invention, there is provided an inspection method for inspecting an object on which a specific pattern is periodically and repetitively formed along a predetermined direction, comprising the steps of: picking-up an image of the object using not less than three gray levels; and obtaining formation information of the specific pattern by statistically analyzing a difference between a raw image obtained as an image pick-up result obtained in the image picking-up step, and a reference image.

According to this method, since the difference between the raw image which is an image pick-up result of an object picked-up as multi-gray level data, and the reference image is statistically analyzed to obtain the formation information of the specific pattern, the formation information of the specific pattern can be obtained by effectively using information contained in the multi-gray level image. Hence, the formation state of periodic repetitive patterns on the object can be accurately inspected.

In the inspection method of the present invention, the step of obtaining the formation information comprises: generating data points, which are defined at as data sets of gray levels at identical positions in said raw and reference images, in a coordinate space which has coordinate axes corresponding to values of the gray levels in said raw and reference images; and obtaining pattern formation information, based on a distribution of said data points in said coordinate space.

In the inspection method of the present invention, upon obtaining the formation information, (N−1) (N is an integer equal to or larger than 2) shift images are obtained by shifting the raw image obtained as the image pick-up result in the image pick-up step by integer multiples of a repetition period in a repetition direction of the specific pattern in the image pick-up result; sets of gray levels at identical positions in N images including the raw image and (N−1) shift images are defined as data points, and data points corresponding to positions in overlapping regions of the N images are plotted in an N-dimensional coordinate space; and pattern formation information of the object is obtained on the basis of a state of a distribution of the data points in the N-dimensional coordinate space.

In such case, based on the raw image which is obtained by picking-up the object and has three or more gray levels, (N−1) shift images are obtained by shifting the raw image in the repetition direction by integer multiples of the repetition period of the specific pattern. Sets of gray levels at identical positions of N images consisting of the raw image and (N−1) shift images are defined as data points in the N-dimensional coordinate space, and data points at respectively positions in overlapping regions of the N images are plotted in the N-dimensional coordinate space.

The plotted data points are distributed around a straight line or a curve (to be generally referred to as an "expectation line" hereinafter) formed by a set of data points of those similarly plotted in an expectation pattern (to be referred to as "expectation data points" hereinafter). When, for example, repetitive patterns formed are exactly the same, and are expected to be simultaneously picked up under identical conditions, the expectation line as a set of expectation data agrees with a straight line (to be referred to as a "reference line" hereinafter) which is a set of points having identical coordinate values in the N-dimensional coordinate. In such data point distribution, if a region of pattern defects is only a portion of the overall region, most of errors from the expectation line are probably contingency errors. That is, most of errors from the expectation line are considered as accidental events.

Therefore, by statistically analyzing the data point distribution state in the N-dimensional coordinate space as a probably distribution, pattern formation information that pertains to pattern defects on the object can be obtained. The N-dimensional coordinate position of a data point completely reflects multi-gray level information at respective points of the multi-gray level images, and the pattern formation information based on the relationship between the expectation pattern and image pick-up result is obtained in practice by analyzing a distribution around points on the expectation line as maximum likelihood estimates, thus accurately inspecting the pattern formation state of the object.

Upon obtaining the shift image, the repetition direction and period in the image pick-up result are obtained by analyzing the raw image; and the (N−1) shift images are obtained using the obtained repetition direction and period.

Also, upon obtaining the formation information, an Nth-order joint probability density function is estimated from the distribution of the data points in the N-dimensional coordinate space, and a reference occurrence frequency at each coordinate position in the N-dimensional coordinate space is computed using the Nth-order joint probability density function; a relationship between the reference occurrence frequency and an actual occurrence frequency at each coordinate position in the N-dimensional coordinate space is computed; and the pattern formation information of the object is obtained on the basis of the computed relationship.

In this case, the reference occurrence frequency can be used as an expectation value of a occurrence frequency at each coordinate position in the N-dimensional coordinate space when the Nth-order joint probability density function is used; and the relationship between the reference and the actual occurrence frequencies can use ratio between the reference and actual occurrence frequencies. That is, the expectation value of the occurrence frequency as a maximum likelihood estimate at each coordinate position when the estimated Nth-order joint probability density function is used is defined as a reference occurrence frequency. When the ratio of the actual occurrence frequency to the reference occurrence frequency falls within a predetermined range, no pattern defects are estimated to be present; and when the ratio of the actual occurrence frequency to the reference occurrence frequency falls outside the predetermined range, pattern defects are estimated to be present.

The reference occurrence frequency can be used as at least one of upper and lower limit values of a confidence interval according to a predetermined statistical confidence, which pertains to an expectation value of a occurrence frequency at each coordinate position in the N-dimensional coordinate space when the Nth-order joint probability density function is used, and the relationship between the reference and actual occurrence frequencies can be use difference between the reference and actual occurrence frequencies. In such case, the respective amount of the reference and actual occurrence frequencies are compared using the reference occurrence frequency as at least one of the upper and lower limit values of the confidence interval according to the predetermined statistical confidence, which pertains to the expectation value of the occurrence frequency as the maximum likelihood estimate at each coordinate position upon using the estimated Nth-order joint probability density function. For example, if the reference occurrence frequencies define the upper and lower limit values of the confidence interval and the actual occurrence frequency falls within the confidence interval, no pattern defects are estimated to be present; if the actual occurrence frequency falls outside the confidence interval, pattern defects are estimated to be present. If a coordinate position where the actual occurrence frequency is larger than the upper limit value of the confidence interval is found, pattern defects are estimated to be present, and the data points at that coordinate position include a data point according to the pattern defects. On the other hand, if a coordinate position where the actual occurrence frequency is smaller than the lower limit value of the confidence interval is found, it is estimated that a coordinate position including a data point according to actual pattern defects cannot be specified but some pattern defects are present anywhere else.

In the inspection method of the present invention using the confidence interval, the confidence interval can be obtained under the assumption that the probability of occurrence at each coordinate position in the N-dimensional coordinate space complies with a binomial distribution which uses the expectation value as an average value. When the number of data points is sufficiently large, the confidence interval can be obtained under the assumption that the probability of occurrence at each coordinate position in the N-dimensional coordinate space complies with a Poisson distribution which uses the expectation value as an average value.

In the inspection method of the present invention using the Nth-order joint probability density function, the Nth-order joint probability density function can be estimated as a mixture of a plurality of N-dimensional normal distribution type probability density functions. In this manner, it is particularly effective to estimate the Nth-order joint probability density function as a mixture of a plurality of N-dimensional normal distribution type probability density functions, when the distribution of errors of data points from expectation data points complies with a normal distribution type. When the probability density functions of errors of data points are known, they can be used. On the other hand, when the probability density functions of errors of data points are unknown, it is rational to estimate the normal distribution type, which is a most prevalent probability density function, as the Nth-order joint probability density function.

Note that the Nth-order joint probability density function can be estimated by dividing the N-dimensional coordinate space into a plurality of partial spaces by at least one (N−1)-dimensional plane which is perpendicular to a reference line as a set of points having equal coordinate values in the N-dimensional coordinate space; estimating N-dimensional normal distribution type probability density functions in units of partial spaces from the data points in each of the partial spaces; and computing a weighted sum of the N-dimensional normal distribution type probability density functions in units of partial spaces depending on the corresponding numbers of data points.

In such case, when the overall data point distribution is formed around a plurality of expectation data points present on the expectation line, the N-dimensional coordinate space is divided into a plurality of appropriate partial spaces each including one expectation data point, thus estimating the N-dimensional normal distribution type probability density function of each partial space. It is desirable to divide the coordinate space into a plurality of partial spaces on (N−1)-dimensional planes perpendicular to the expectation line. But (a) the expectation line is unknown and (b) the expectation line nearly agrees with the reference line since each repetitive pattern is picked up under substantially the same image pick-up condition. For these reasons, the N-dimensional coordinate space is divided by (N−1)-dimensional planes perpendicular to the reference line as a set of points with equal coordinate values in the N-dimensional coordinate space.

By computing the sum of N-dimensional normal distribution type probability density functions of the individual partial spaces, which are weighted depending on the numbers of corresponding data points, the N-dimensional normal distribution type probability density function of the entire data point distribution is computed. As a result, the N-dimensional normal distribution type probability density function of the entire data point distribution can be accurately estimated with a smaller computation volume than upon computing it at once using all data points.

Note that the N-dimensional normal distribution type probability density functions corresponding to the plurality of partial spaces can be estimated as Nth-order joint probability density functions having centers on the reference line for the aforementioned reasons (a) and (b) In this case, although the estimation accuracy drops slightly, the computation volume can be further reduced.

The N-dimensional coordinate space can be divided into the plurality of partial spaces to maximize the likelihood of the Nth-order joint probability density function estimated for each of the plurality of partial spaces as a whole.

The Nth-order joint probability density function can be estimated by dividing the N-dimensional coordinate space into a plurality of partial spaces by a plurality of (N−1)-dimensional planes which are perpendicular to a reference line as a set of points having equal coordinate values in the N-dimensional coordinate space; mapping the data points in the plurality of partial spaces onto the (N−1)-dimensional planes perpendicular to the reference line; computing (N−1)-dimensional normal distribution type probability density functions for the plurality of partial spaces on the basis of the distributions of the mapped data points on the (N−1)-dimensional planes; and computing a weighted sum of the N-dimensional normal distribution type probability density functions depending on the corresponding numbers of data points. In such case, since the joint probability density function is computed not as the N-dimensional normal distribution type probability density function but as the (N−1)-dimensional normal distribution type probability density function, the computation volume can be reduced although the estimation accuracy generally lowers. When the data point distribution in each partial space is nearly cylinder-symmetric to have the reference line as the central line, since the computation volume can be greatly reduced while maintaining high estimation accuracy of the Nth-order joint probability density function of the entire data point distribution, the formation state of repetitive patterns on the object can be inspected very quickly while maintaining high inspection accuracy.

In the inspection method of the present invention, upon obtaining the formation information, a first probability density function which pertains to occurrence probabilities of relationship data is estimated on the basis of a distribution of the relationship data of gray levels in the raw image obtained as the image pick-up result in the image pick-up step and the reference image at identical positions; a second probability density function that pertains to occurrence frequencies of individual values of the relationship data is estimated under an assumption that a probability distribution of the relationship data complies with the first probability density function, and estimating reference occurrence frequencies of the individual values of the relationship data; abnormal relationship data candidates which are estimated to be abnormal relationship data, which have occurrence frequencies in the distribution of the relationship data that do not comply with the first probability density function at a predetermined confidence, are extracted on the basis of the second probability density function, the reference occurrence frequencies, and occurrence frequencies of the individual values of the relationship data in the distribution of the relationship data; and a first probability that each of the abnormal relationship data candidate is the abnormal relationship data is estimated.

With this, using a raw image having three or more gray levels obtained by picking-up an object in the image pick-up step, relationship data (e.g., the difference, ratio, and the like of gray levels at identical positions of the raw and reference images) of gray levels at identical positions of the raw and reference images are obtained. The distribution of such relationship data results from formation errors of patterns since a region of pattern defects is normally only a portion of the overall region. Most generations of relationship data are considered as probability phenomena. Hence, by considering generations of relationship data as probability phenomena, a first probability density function that pertains to probabilities of occurrence of relationship data is estimated. Subsequently, reference occurrence frequencies of respective relationship data values are estimated by estimating a second probability density function that pertains to the occurrence frequencies of relationship data in respective relationship data values, when the probability distribution of the relationship data complies with the first probability density function, i.e., when maximum likelihood estimates of probabilities of occurrence of relationship data values are obtained by the first probability density function.

Then, abnormal relationship data candidates which are estimated to be abnormal relationship data, in which the occurrence frequencies in the relationship data distribution do not comply with the first probability density function with a predetermined confidence, are extracted on the basis of the estimation result in the second estimation step and the occurrence frequencies of relationship data values in the relationship data distribution. After the abnormal relationship data candidates are extracted, the probability that each abnormal relationship data candidate is abnormal relationship data (to be referred to as an "abnormal probability" hereinafter) is computed in the abnormal probability computation step.

The abnormal probability is statistically appropriate since it is computed by executing statistical processes on the basis of raw image data obtained by image picking-up. Hence, pattern defects can be logically found by checking based on the abnormal probability if each abnormal relationship data candidate is abnormal relationship data that reflects pattern defects. For this reason, the formation state of periodic repetitive patterns on the object can be accurately inspected.

Also, upon checking if each abnormal relationship data candidate is abnormal relationship data, since raw image data is processed as multi-valued data without executing binarization immediately after the difference between the raw and shift images is computed unlike in the prior art, so-called rounding errors generated by arithmetic processes after binarization can be prevented from being accumulated, and whether or not each abnormal relationship data candidate is abnormal relationship data can be accurately checked.

As described above, the relationship data can use one of a difference and ratio between pixels in the raw and reference images, as described above. Either the difference or ratio can be used as relationship data which is used to accurately find any pattern defects.

The reference image can be either a predetermined image or a shift image obtained by shifting the raw image by an integer multiple of a repetition period in a repetition direction of the specific pattern in the image pick-up result. When the shift image is used, a product of the first probability and a second probability that relationship data which pertains to a position in the shift image corresponding to the position of the abnormal relationship data candidate in the raw image is the abnormal relationship data is computed; and appropriateness of determining that the abnormal relationship data candidate is the abnormal relationship data is evaluated based on the probability product.

In such case, after the abnormal probability of the abnormal relationship data candidates is computed as described above, the product of that probability and the abnormal probability of relationship data associated with the position in the shift image corresponding to the position of the abnormal relationship data candidate in the raw image is computed in the probability product computation step. Whether or not each abnormal relationship data candidate is abnormal relationship data is checked based on the computed product value in the evaluation step. That is, if the abnormal probability product value associated with a given abnormal relationship data candidate is larger than a predetermined threshold value, it is determined that the abnormal relationship data candidate is abnormal relationship data; if the abnormal probability product value associated with a given abnormal relationship data candidate is equal to or smaller than the predetermined threshold value, it is determined that the abnormal relationship data candidate is not abnormal relationship data. As a result, when both the abnormal relationship data candidate and the abnormal probability of its corresponding relationship data are large to some extent, i.e., when it is regarded that pattern defects are reflected in both the abnormal relationship data candidate and its corresponding relationship data, it is determined that the abnormal relationship data candidate is abnormal relationship data. Hence, the positions of pattern defects upon duplicated generation of abnormal relationship data candidates associated with a pixel corresponding to the pattern defects, which inevitably occurs since the reference image is used as a shift image, can be prevented from being additionally recognized. Therefore, the formation state of periodic repetitive pattern on the object can be accurately inspected.

The reference image can use at least one shift image obtained by shifting the raw image in the repetition direction in the image pick-up result by an integer multiple of the repetition period, and the relationship data can use vector data having as components gray levels at identical positions in the raw image and at least one shift image. Even in such case, the vector data as the relationship data is multi-valued data that completely reflects multi-gray level information at each point of a multi-gray level image, abnormal relationship data candidates are extracted by statistically processing the distribution of such multi-valued data, and the abnormal probabilities of the abnormal relationship data candidates are computed. Therefore, statistically appropriate abnormal probabilities can be obtained while preventing so-called rounding errors produced by arithmetic processes after binarization.

When the reference image is used as a shift image, the shift image can be obtained using the repetition direction and period in the image pick-up result obtained by analyzing the raw image.

Also, the first probability function can be estimated as a normal distribution type probability density function. In this way, it is particularly effective to estimate the first probability density function as a normal distribution type probability density function when the distribution of errors complies with a normal distribution. When the probability density function of errors is known, it can be used. On the other hand, when the probability density function of errors is unknown, it is rational to estimate it as a normal distribution type probability density function, which is the most prevalent probability density function.

An upper limit value of a confidence interval corresponding to a predetermined statistic confidence based on the second probability density function can be obtained as the reference occurrence frequency, and the abnormal relationship data candidates can be extracted in the extraction step on the basis of the reference occurrence frequencies and the occurrence frequencies of individual values of the relationship data. In such case, relationship data having a relationship data value, the actual occurrence frequency of which has exceeded the upper limit value of the confidence interval of the occurrence frequencies obtained from the second probability density function, is extracted as an abnormal relationship data candidate. Therefore, abnormal relationship data can be statistically logically extracted.

When the relationship data value has an actual occurrence frequency which is lower than the lower limit value of the confidence interval, it is estimated that pattern defects are present somewhere. In this case, it is not estimated that abnormal relationship data is included in relationship data having that relationship data value, but it is merely estimated that pattern defects are present somewhere the entire image. For this reason, upon detecting the relationship data value having an actual occurrence frequency which is lower than the lower limit value of the confidence interval, abnormal relationship data candidates are inhibited from being extracted.

In this case, the second probability density function can be estimated as one of a binomial distribution probability density function and a Poisson distribution probability density function. If the number of relationship data is sufficiently large, the second probability density function can be estimated to comply with a Poisson distribution which has as an average value the occurrence frequency when the first probability density function is a maximum likelihood estimate of the probability of occurrence of each relationship data value. If the number of relationship data is not sufficiently large, the second probability density function can be estimated to comply with a binomial distribution when the first probability density function is a maximum likelihood estimate of the probability of occurrence of each relationship data value.

Note that the formation position of a specific pattern on the object to be inspected is not particularly limited. But when the specific pattern is formed on the surface of the object, the formation state of periodic repetitive patterns on the object can be accurately inspected using image data obtained by a normal image pick-up unit.

According to the second aspect of the present invention, there is provided an inspection apparatus for inspecting an object on which a specific pattern is periodically and repetitively formed along a predetermined direction, comprising: an image pick-up unit for picking-up an image of the object using not less than three gray levels; and a statistical processing unit for obtaining formation information of the specific pattern by statistically analyzing a difference between a raw image of an image pick-up result obtained by the image pick-up unit, and a reference image.

According to this apparatus, since the statistical processing unit statistically analyzes the difference between the raw image as the image pick-up result of the object which is picked up as multi-gray level data by the image pick-up unit, and the reference image so as to obtain the formation information of the specific pattern, the formation information of the specific pattern is obtained by effectively utilizing information contained in the multi-gray level image. Hence, the formation state of periodic repetitive patterns on the object can be accurately detected.

In the inspection apparatus of the present invention, the statistical processing unit can comprise: an image shift unit for obtaining (N−1) shift images by shifting the raw image as the image pick-up result obtained by the image pick-up unit by integer multiples of a repetition period in a repetition direction of the specific pattern in the image pick-up result; and a pattern formation information arithmetic unit for defining as data point sets of gray levels at identical positions in N images including the raw image and (N−1) shift images, plotting data points corresponding to positions in overlapping regions of the N images in an N-dimensional coordinate space, and obtaining pattern formation information of the object on the basis of a state of a distribution of the data points in the N-dimensional coordinate space.

In such case, the image shift unit obtains (N−1) shift images by shifting the raw image by integer multiples of the repetition period in the repetition direction of the specific pattern on the basis of the raw image obtained by the image pick-up unit and having three or more gray levels. The pattern formation information arithmetic unit defines sets of gray levels at identical positions of N images consisting of the raw image and (N−1) shift images as data points in the N-dimensional coordinate space, plots data points at respectively positions in an overlapping region of the N images in the N-dimensional coordinate space, and obtains the pattern formation information of the object from the state of the data point distribution in the N-dimensional coordinate space.

The image shift unit can comprise: a repetition information computation unit for obtaining the repetition direction and period in the image pick-up result by analyzing the raw image; and a shift computation unit for obtaining the (N−1) shift images using the repetition direction and period obtained by the repetition information arithmetic unit.

The pattern formation information computation unit can comprise: a reference frequency arithmetic unit for estimating an Nth-order joint probability density function from the distribution of the data points in the N-dimensional coordinate space, and computing a reference occurrence frequency at each coordinate position in the N-dimensional coordinate space using the Nth-order joint probability density function; and a pattern formation information arithmetic unit for computing a ratio between the reference occurrence frequency and an actual occurrence frequency at each coordinate position in the N-dimensional coordinate space, and obtaining the pattern formation information of the object on the basis of the computed ratio.

In the inspection apparatus of the present invention, the pattern formation information computation unit can obtain confidence information indicating if the specific pattern information is formed on each of formation regions of the specific pattern on the object as the pattern formation information of the object.

The apparatus can further comprise a defect position arithmetic unit for obtaining a candidate position of at least one of foreign matter and a pattern defect on the object on the basis of the confidence information obtained by the pattern formation information arithmetic unit and positions on the object of the data points plotted in the N-dimensional coordinate space.

In the inspection apparatus of the present invention, the statistical processing unit can comprise: an estimation unit for estimating a first probability density function which pertains to occurrence probabilities of relationship data on the basis of a distribution of the relationship data of gray levels in the raw image obtained as the image pick-up result by the image pick-up unit and the reference image at identical positions, estimating a second probability density function that pertains to occurrence frequencies of the relationship data of individual values of the relationship data under an assumption that a probability distribution of the relationship data complies with the first probability density function, and estimating reference occurrence frequencies of the individual values of the relationship data; an extraction unit for extracting abnormal relationship data candidates which are estimated to be abnormal relationship data, which have occurrence frequencies in the distribution of the relationship data that do not comply with the first probability density function at a predetermined confidence, on the basis of the estimation results of the estimation unit and occurrence frequencies of the individual values of the relationship data in the distribution of the relationship data; and an abnormal probability computation unit for computing a first probability that each of the abnormal relationship data candidate is the abnormal relationship data.

In such case, the estimation unit estimates a first probability density function that pertains to occurrence probabilities of relationship data by obtaining relationship data of gray levels in the raw and reference images at identical positions using the raw image having three or more gray levels obtained by the image pick-up unit, and estimates a second probability density function that pertains to the occurrence frequencies of relationship data in respective relationship data values, when the probability distribution of the relationship data complies with the first probability density function. Subsequently, the extraction unit extracts abnormal relationship data candidates which are estimated to be abnormal relationship data, in which the occurrence frequencies in the relationship data distribution do not comply with the first probability density function with a predetermined confidence. The abnormal probability computation unit then computes abnormal probabilities of the abnormal relationship data candidates. Hence, pattern defects can be accurately inspected.

Note that the reference image is a shift image obtained by shifting the raw image by an integer multiple of a repetition period in a repetition direction of the specific pattern in the image pick-up result, and the apparatus can further comprise an image shift unit for obtaining the shift image by shifting the raw image by an integer multiple of the repetition period in the repetition direction; a probability product computation unit for computing a probability product of the first probability and a second probability that relationship data which pertains to a position in the shift image corresponding to the position of the abnormal relationship data candidate in the raw image is the abnormal relationship data; and an evaluation unit for evaluating based on the probability product appropriateness that the abnormal relationship data candidate is the abnormal relationship data.

When the reference image is used as a shift image, the image shift unit can comprise: a repetition information computation unit for computing the repetition direction and period in the image pick-up result by analyzing the raw image; and a shift computation unit for obtaining the shift image using the repetition direction and period obtained by the repetition information computation unit.

BRIEF DESCRIPTION OF THE DRAWINGS

FIG. 6 is a flow chart showing the process for computing the confidence upon forming repetitive patterns;

DESCRIPTION OF THE PREFERRED EMBODIMENTS

<<First Embodiment>>

The first embodiment of the present invention will be described hereinafter with reference to FIGS. 1 to 12C.

Figure 1:
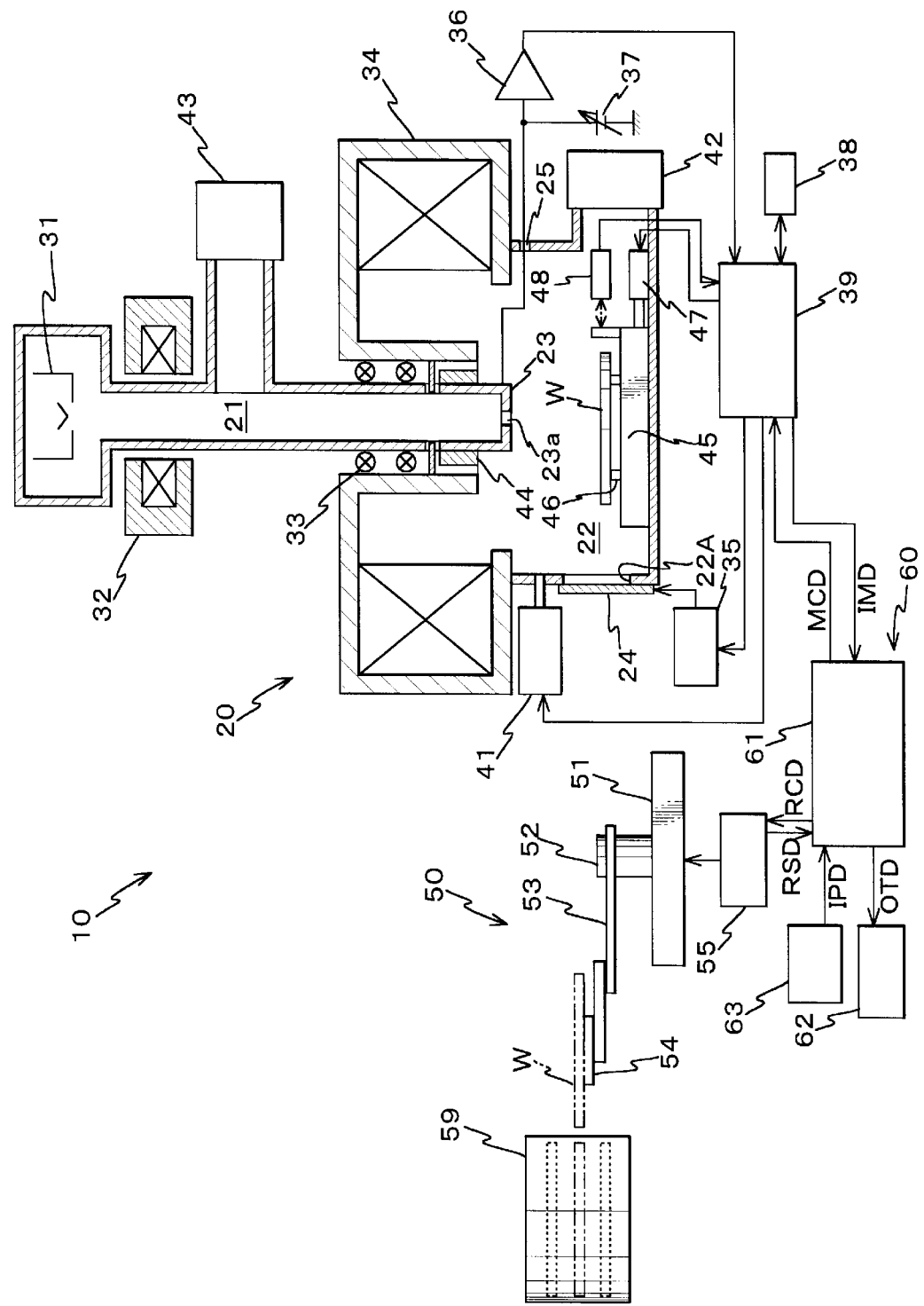
FIG. 1 is a schematic diagram showing the arrangement of an inspection apparatus according to the first embodiment.

FIG. 1 shows a schematic arrangement of an inspection apparatus 10 according to an embodiment. The inspection apparatus 10 comprises an image pick-up unit 20 for picking-up the surface of a wafer W as an object on which repetitive patterns are formed, a convey unit 50 for conveying the wafer W, and a processing control system 60 for systematically controlling the overall inspection apparatus 10 and processing surface image data of the wafer W, as shown in FIG. 1. A cassette table (not shown) is provided on the left side of the convey unit 50 in FIG. 1, and a cassette 59 for nearly horizontally stacking/storing a plurality of wafers W is placed on the cassette table.

As the image pick-up unit 20, an environment-controlled scanning electron microscope is used in this embodiment.

The image pick-up unit 20 comprises a vacuum chamber 21 that houses an electron gun 31, and a sample chamber 22 which contacts the vacuum chamber 21 via a pressure limiting aperture plate 23. The electron gun 31 is arranged in the upper portion of the vacuum chamber 21, a condenser lens 32 is arranged outside the relatively upper central portion of the vacuum chamber 21, and an electromagnetic deflector 33 is arranged outside the lower portion of the vacuum chamber 21. Around the electromagnetic deflector 33, an objective lens 34 made up of an electromagnetic lens electrically insulated by the pressure limiting aperture plate 23 and an insulator 44 is arranged.

In FIG. 1, the vacuum chamber 21 is conceptually illustrated as a single room, but is constructed by a plurality of (e.g., three) rooms partitioned by pressure limiting aperture plates (not shown) in practice, and each room is differentially evacuated by a vacuum pump. The electron gun 31 is arranged in the room with the highest degree of vacuum.

A supply source 41 supplies gas having an electron multiplying effect (e.g., steam) to the interior of the sample chamber 22, and the pressure of the gas in the sample chamber 22 is maintained at around 10 to 5,000 Pa by a vacuum pump 42. An X-Y stage 45 is arranged inside the sample chamber 22, and moves in two-dimensional directions in a plane perpendicular to the page of FIG. 1. When a wafer W is loaded by an arm 53 with its pattern formation surface facing up, as will be described later, and is placed on the X-Y stage 45, secondary electrons produced by the wafer W are multiplied by the gas supplied from the supply source 41.

The gas in the sample chamber 22 leaks into the vacuum chamber 21 via an aperture 23a of the pressure limiting aperture plate 23, but the pressure of gas in the vacuum chamber 21 is maintained at a higher degree of vacuum (lower pressure) than the sample chamber 22 by a vacuum pump 43 (the degree of vacuum gradually increases by differential evacuation in practice).

On the left wall (FIG. 1) of the sample chamber 22, an opening 22A through which the wafer W and arm 53 are inserted/removed is formed, and which is opened/closed by a door 24 which is driven by a motor 35. The door 24 is controlled to open/close by a controller 39. Note that a high-speed shutter is used as the door 24.

On the X-Y stage 45, three vertically movable support pins 46 are provided. With these support pins 46, the wafer W which has been conveyed above the X-Y stage 45 with its pattern forming surface facing up by the arm 53, as will be described later, is placed on the X-Y stage 45. The X-Y stage 45 is driven by a driving unit 47, and its position is always detected by a laser interferometer 48. The output signal from the laser interferometer 48 is input to the controller 39.

In this embodiment, the pressure limiting aperture plate 23 also serves as a secondary electron detector (detection electrode), and is applied with a positive voltage (with respect to the wafer W) from a variable voltage source 37 via an insulating hermetic seal 25 formed on the side wall of the sample chamber 22.

For this reason, upon picking-up the pattern formation surface of the wafer W, an electron beam emitted by the electron gun 31 in the vacuum chamber 21 is focused on the surface of the wafer W via the aperture 23a of the pressure limiting aperture plate 23, and the focused electron beam is scanned on the surface of the wafer W by the electromagnetic deflector 33. At this time, secondary electrons released from the wafer W are multiplied by low-pressure gas such as steam in the sample chamber 22 by an electric field from the pressure limiting aperture plate 23 as the secondary electron detector, and positive ions (cations) produced as a result of multiplication are absorbed by the wafer W to neutralize negative charges of the wafer W produced upon irradiation with the electron beam. The multiplied secondary electrons are detected by the pressure limiting aperture plate 23, and a secondary electron signal obtained from the pressure limiting aperture plate 23 is amplified by a preamplifier 36.

The controller 39 integrates and A/D-converts the amplified secondary electron signal, then stores an image (secondary electron image) in an image memory 38, and outputs stored image data IMD to the processing control system 60. The controller 39 controls the position of the X-Y stage 45 via the driving unit 47 and controls vertical movement of the support pins 46 on the basis of control data MCD from the processing control system 60. The controller 39 systematically controls the entire image pick-up unit (environment-controlled scanning electron microscope) 20.

The convey unit 50 has a base 51, a driving unit 52 provided on the base 51, and a extensible arm 53 which is turned and vertically moved by the driving unit 52. A chuck 54 for the wafer W is provided to the distal end of the arm 53. The convey unit 50 comprises a controller 55, which controls the overall convey unit 50 in accordance with control data RCD from the processing control system 60.

The processing control system 60 comprises a processing control unit 61 for processing control data, and processing surface image data of the wafer W obtained by the image pick-up unit 20 to obtain pattern formation information that pertains to pattern defects on the wafer surface, and a display unit 62 and input unit (keyboard and the like) 63 connected to the processing control unit 61. The display unit displays the image pick-up result (e.g., secondary electron image) of the image pick-up unit 20, the processing result of the image pick-up result data, and the like, and the input unit 63 allows the operator to input commands, various processing conditions, and the like to the processing control unit 61.

Figure 2:
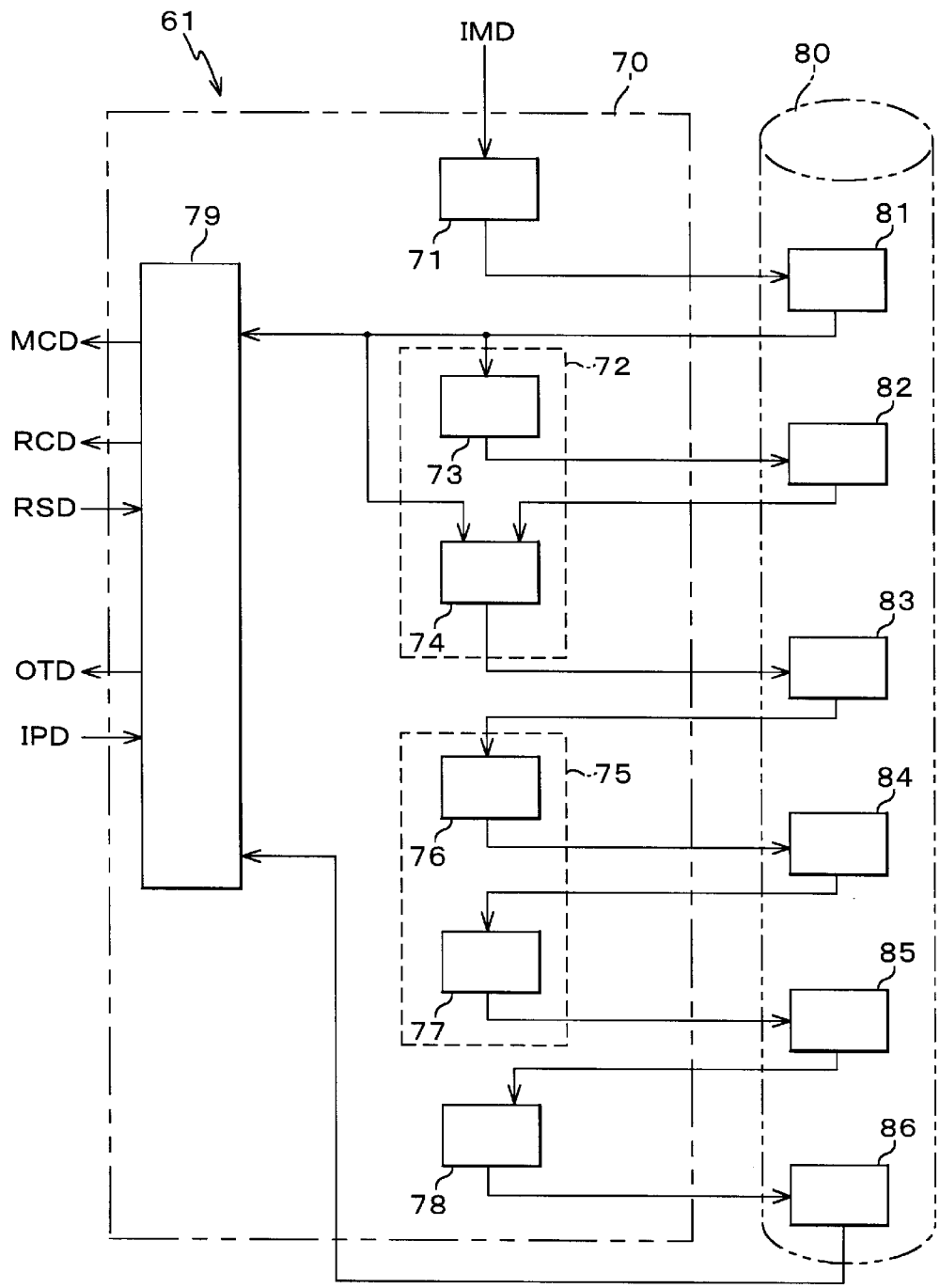
FIG. 2 is a diagram showing the arrangement of a processing control system in the first embodiment.

The processing control unit 61 comprises a data processing unit 70 and storage unit 80, as shown in FIG. 2.

The data processing unit 70 comprises (a) a control unit 79 for controlling the operation of the image pick-up unit 20 by supplying, e.g., image pick-up unit control data MCD to the controller 39 of the image pick-up unit 20, and controlling the operation of the convey unit 50 by supplying, e.g., convey unit control data RCD to the controller 55 of the convey unit 50, (b) a picked-up image data acquisition unit 71 for acquiring picked-up image data IMD sent from the image pick-up unit 20, (c) an image shift unit 72 for obtaining a raw image from the acquired picked-up image data, and obtaining a shift image by shifting the raw image by a repetition period in the repetition direction of patterns in the raw image, (d) a pattern formation information computation unit 75, while defining sets of gray levels of the raw and shift images at identical positions as data points in a two-dimensional space (to be referred to as a "grayscale space" hereinafter), and obtaining pattern formation information on the surface of the wafer W on the basis of the state of a data point distribution obtained by placing data points corresponding to respective positions of overlapping regions of the raw and shift images in the grayscale space, and (e) a defect position arithmetic unit 78 for obtaining a candidate position of pattern defects on the surface of the wafer W. The control unit 79 receives state information RSD that pertains to turning, vertical movement, and extensible movement of the arm 53 from the convey unit 50, and receives information IPD input by the operator from the input unit 63. Furthermore, the control unit 79 supplies output data OTD as display data to the display unit 62.

The image shift unit 72 has (i) a repetition information computation unit 73 for obtaining the repetition direction and period of patterns in the raw image by analyzing the raw image, and (ii) a shift computation unit 74 for obtaining a shift image using the repetition direction and period obtained by the repetition information computation unit 73. The pattern formation information computation unit 75 has (i) a reference frequency arithmetic unit 76 for computing the reference occurrence frequency at each coordinate position of the grayscale space by estimating a second-order joint probability density function from the data point distribution in the grayscale space, and (ii) a pattern formation information arithmetic unit 77 for computing the relationship between the reference and actual occurrence frequencies at each coordinate position of the grayscale space, and computing pattern formation information on the surface of the wafer W on the basis of the computed relationship. The operations of units that construct the processing control unit 61 will be described later.

The storage unit 80 has a picked-up image data storage area 81, a repetition information storage area 82, an image shift information storage area 83 for storing raw and shift image data, a reference occurrence frequency storage area 84 for storing the estimated second-order joint probability density function and the reference occurrence frequency at each coordinate position in the grayscale space, a pattern formation information storage area 85 for storing pattern formation information, and a defect candidate position information storage area 86 for storing candidate position information of pattern defects.

In this embodiment, the processing control unit 61 is constructed by combining various units. Alternatively, the processing control unit 61 may be constructed as a computer system, and the function of the units that construct the data processing unit 70 may be implemented by a program installed in the processing control unit 61.

Inspection of a wafer W by the inspection apparatus 10 with the aforementioned configuration will be explained below.

Assume that a plurality of (three in FIG. 1) wafers W to be inspected are stored in the cassette 59.

Figure 3:
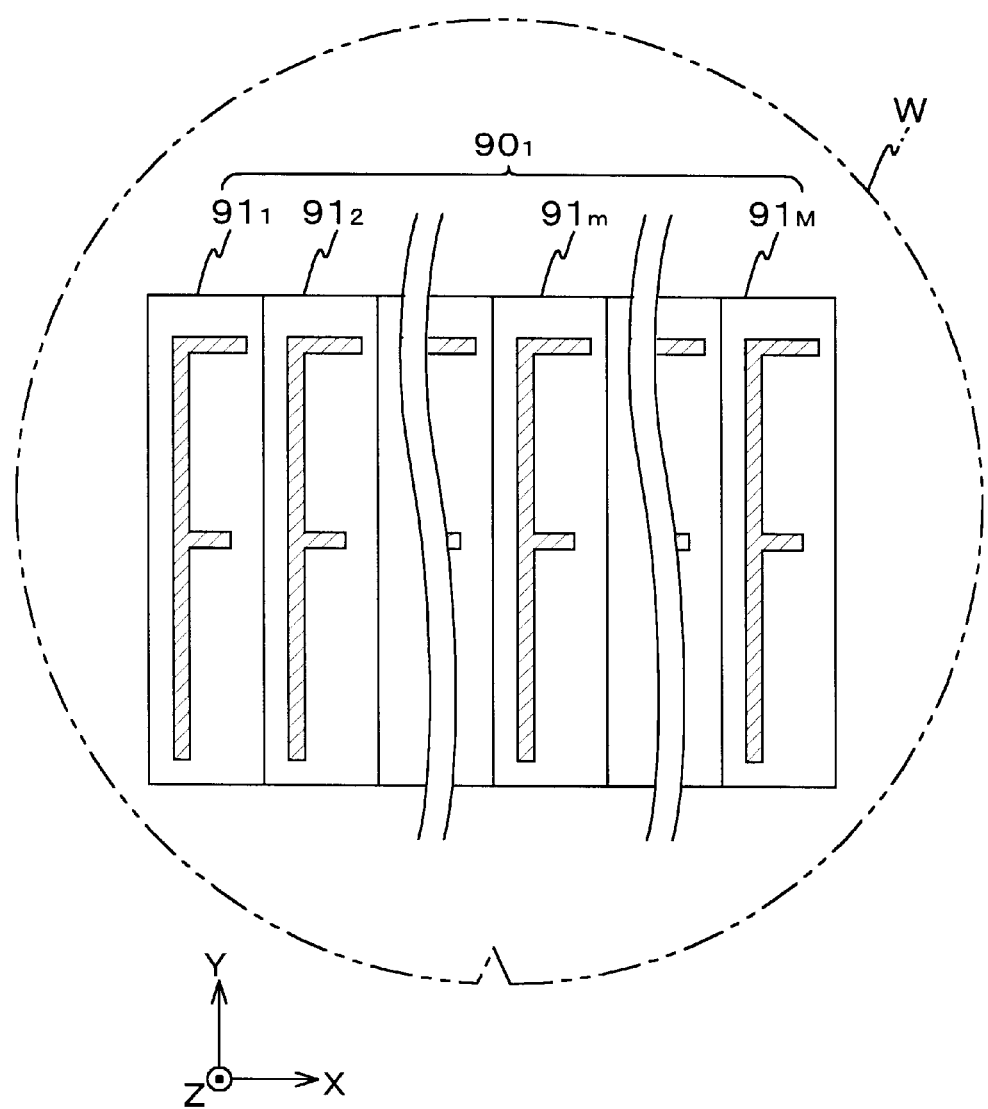
FIG. 3 shows an example of repetitive patterns.

Also, assume that, in this embodiment, repetitive patterns are formed on a repetitive pattern region $90_1$, on the surface of the wafer W to be inspected, as shown in FIG. 3. That is, in the repetitive pattern region $90_1$, unit pattern regions $91_1$, to $91_M$ which have the same X-width and on each of which an identical unit pattern made up of line and space patterns are formed line up in the X-direction.

In this embodiment, the unit patterns are formed on the individual unit pattern regions $91_m$ (m=1 to M) under substantially the same conditions, and are picked up under substantially the same conditions free from, e.g., any gradients of the exposure light amount and image pick-up illumination light amount in the X-Y space.

Furthermore, assume that information as the aforementioned conditions of inspection is input by the operator to the processing control unit 61 (more specifically, control unit 79) via the input unit 63. Based on such input information, inspection of the inspection apparatus 10 of this embodiment starts under the systematic control of the processing control system 60.

The inspection process that pertains to the formation state of repetitive patterns on the surface of the wafer W will be explained below based on the flow chart shown in FIG. 4 while referring to other drawings as needed.

Figure 4:
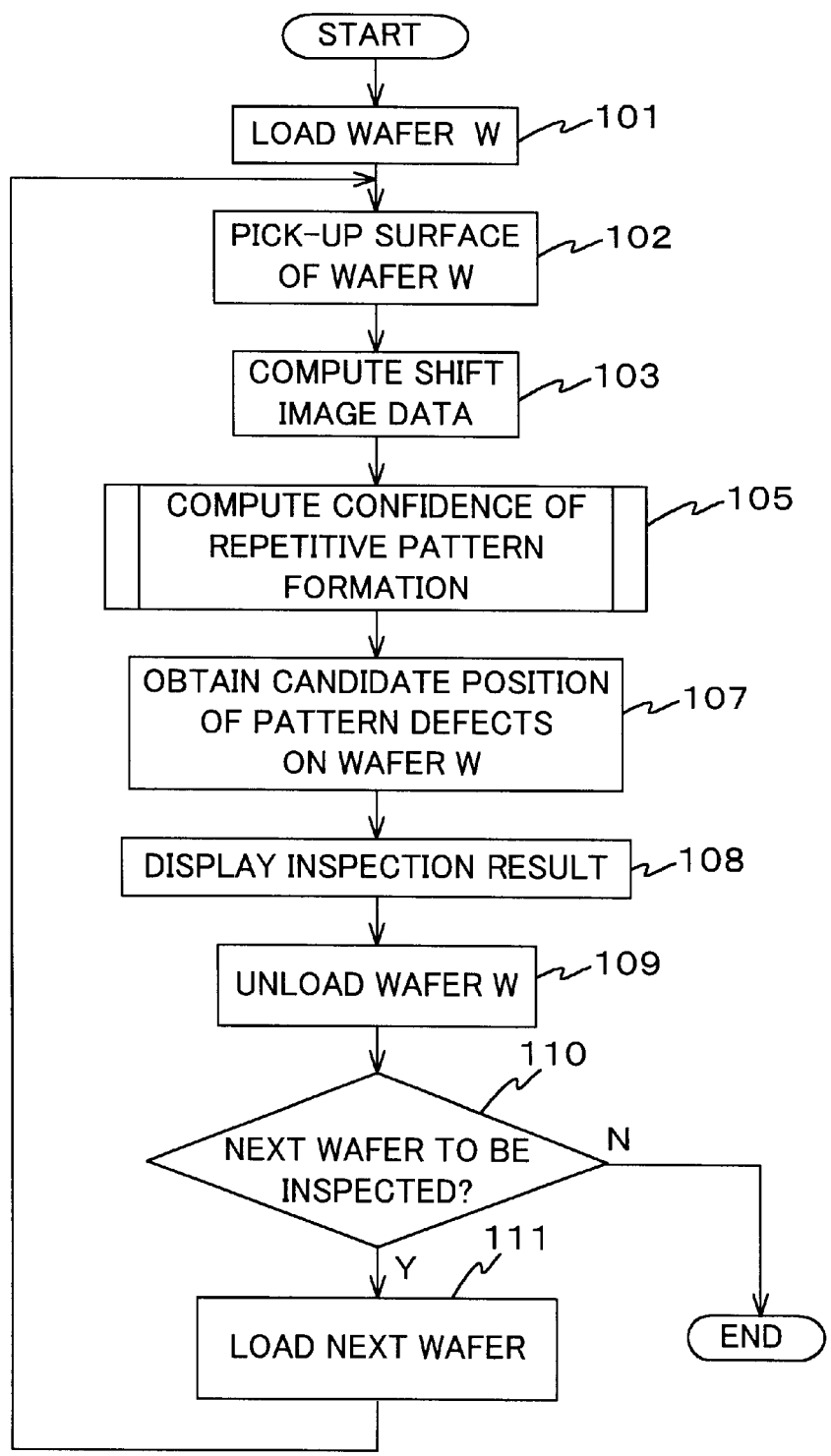
FIG. 4 is a flow chart showing the process for inspecting the formation state of repetitive patterns in the first embodiment.

In step 101 in FIG. 4, one of the wafers W in the cassette 59 is loaded onto the X-Y stage 45 of the image pick-up unit 20. That is, the controller 55 turns the arm 53 in a direction coming out of the page of FIG. 1 via the driving unit 52 on the basis of control data RCD input from the control unit 79. The controller 55 vertically moves the arm 53 via the driving unit 52, and stretches the arm 53 to insert it below a desired wafer W in the cassette 59. The controller 55 raises the driving unit 52 to chuck and hold the wafer W on the chuck 54, and then retracts the arm 53 from the cassette 59. Furthermore, in order to load the wafer W into the image pick-up unit 20, the controller 55 turns the arm 53 toward the image pick-up unit 20 via the driving unit 52. Then, the controller 55 extends the arm 53 toward the image pick-up unit 20. At this time, the motor 35 is driven by the controller 39, and the door 24 moves in a direction to open. Upon movement of the door 24, the opening 22A is opened. The controller 39 inserts the arm 53 into the sample chamber 22 via the opening 22A, and conveys the wafer W above the X-Y stage 45 which stands by at a predetermined transfer position. After the wafer W is conveyed above the X-Y stage 45, the controller 39 moves the three support pins 46 upward. As a result, the lower surface of the wafer W is supported by the support pins 46.

The controller 55 retracts the arm 53 from the sample chamber 22. At the same time, the controller 39 lowers the support pins 46 to place the wafer W on the X-Y stage 45. The controller 39 drives the door 24 to close the opening 22A. At the same time, the controller 39 differentially evacuates the vacuum chamber 21 and sample chamber 22 using the vacuum pumps 43 and 42, and supplies gas having an electron multiplying effect (e.g., steam) into the sample chamber 22, thus setting the gas pressure in the sample chamber 22 at around 10 to 5,000 Pa.

In step 102, the controller 39 controls the position of the X-Y stage on the basis of control data MCD supplied from the control unit 79 so that regions including the aforementioned repetitive pattern region $90_1$ on the surface of the wafer W are scanned in turn with an electron beam from the electron gun 31, while the wafer W is irradiated with the electron beam coming from the electron gun 31. As a result of irradiation with the electron beam, secondary electrons which are generated from the wafer W and are multiplied are detected by the pressure limiting aperture plate 23. A signal that pertains to the detected secondary electrons is amplified by the preamplifier 36, and is then input to the controller 39 as an analog pick-up image signal. The controller 39 integrates the input analog pick-up image signal with a predetermined time constant, A/D-converts the integrated result with 8-bit precision, and stores the converted data as raw image (secondary electron image) data in the image memory 38.

Upon completion of image pick-up of the wafer W by the image pick-up unit 20, the controller 39 outputs the raw image data stored in the image memory 38 to the processing control unit 61 as picked-up image data IMD. In the processing control unit 61, the picked-up image data acquisition unit 71 receives the picked-up image data IMD, and stores it in the picked-up image data storage area 81.

Figure 5A:
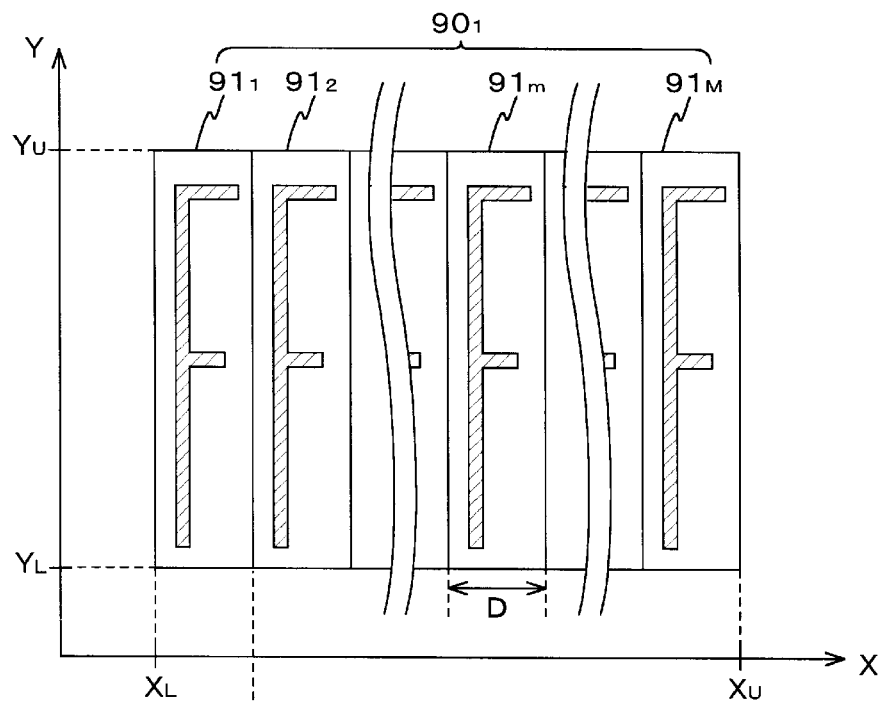
FIGS. 5A and 5B are views showing the relationship between the raw and shift images.

In step 103, the image shift unit 72 computes shift image data on the basis of picked-up image data as raw image data stored in the picked-up image data storage area 81. Upon computing the shift image data, the repetition information computation unit 73 in the image shift unit 72 reads out the raw image data from the picked-up image data storage area 81, and analyzes the raw image data to extract the aforementioned repetitive pattern region $90_1$ and to also extract as repetitive pattern information the repetition direction (X-direction in FIG. 3) and repetition period (the X-width of the unit pattern region $91_m$ in FIG. 3) of the patterns. In this way, the repetitive pattern information which was unknown upon image pick-up can be accurately obtained. FIG. 5A shows an example of the extracted repetitive pattern information. In this embodiment, the following explanation will be given assuming that the repetitive pattern region $90_1$ is a rectangular region defined by X-positions $X_L$ to $X_U$ and Y-positions $Y_L$ to $Y_U$, the repetition direction of the patterns agrees with the X-direction, and the repetition period is D, as shown in FIG. 5A. The repetition information computation unit 73 stores the obtained repetitive pattern information, and image information in the repetitive pattern region $90_1$ in the repetition information storage area 82. Note that $I_1(X, Y)$ represents the gray level (to be also referred to as a "signal level" hereinafter) of each pixel in the image data in the repetitive pattern region $90_1$.

Figure 5B:
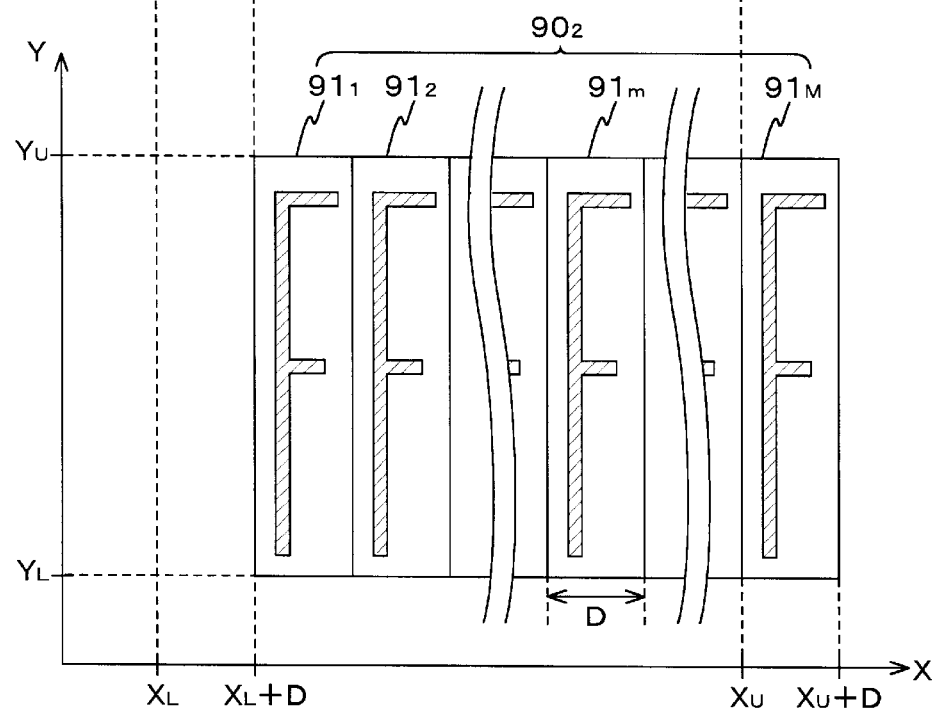

The shift computation unit 74 in the image shift unit 72 reads out the repetitive pattern information and the image data in the repetitive pattern region $90_1$ from the repetition information storage area 82, and computes shift image data by shifting the image data in the repetitive pattern region $90_1$ by the distance D in the X-direction. FIG. 5B shows the shift image obtained in this way. That is, the shift image has a repetitive pattern region $90_2$ which is a rectangular region defined by X-positions $(X_L+D)$ to $(X_U+D)$ and Y-positions $Y_L$ to $Y_U$, the pattern repetition direction which agrees with the X-direction, and the repetition period=D, as shown in FIG. 5B. Note that $I_2(X, Y)$ represents the signal level of each pixel in the image data in the repetitive pattern region $90_2$.

As can be seen from comparison between the raw image shown in FIG. 5A and the shift image shown in FIG. 5B, the pixel at an X-Y coordinate position (X, Y) in the raw image corresponds to the pixel at an X-Y coordinate position (X+D, Y) in the shift image. As a result, the pixel (signal level $I_1(X, Y)$) at the X-Y coordinate position (X, Y) in the raw image and the pixel (signal level $I_2(X, Y)$) at the X-Y coordinate position (X, Y) in the shift image, i.e., a pixel (signal level $I_1(X–D, Y)$) at an X-Y coordinate position (X–D, Y), are located at the X-Y coordinate position (X, Y) ($X_L+D \leq X \leq X_U$, $Y_L \leq Y \leq Y_U$) That is, by superposing the raw and shift images on the X-Y coordinate system, a rectangular region defined by the X-positions ($X_L+D$) to $X_U$ and Y-positions $Y_L$ to $Y_U$ becomes an overlapping region. At the X-Y coordinate position (X, Y), the pixel at the X-Y coordinate position (X, Y) in the raw image overlaps the pixel at the coordinate position (X, Y) in the shift image, i.e., the X-Y coordinate position (X–D, Y) in the raw image. Note that $Q_0$ represents the number of pixels of the overlapping region. Assume that the number $Q_0$ of pixels is a very large value, for example, 512×512.

When the unit pattern is ideally repeated, i.e., identical unit patterns are formed on the unit pattern regions $91_m$, we have:

$$I_1(X, Y) = I_2(X, Y) \quad (1)$$

However, equation (1) does not always hold due to errors generated upon formation patterns or upon image pick-up. When any pattern defects are present, equation (1) does not hold at the position of the pattern defects.

The shift computation unit 74 stores raw image data $I_1(X, Y)$ and shift image data $I_2(X, Y)$ in the image shift information storage area 83 as image shift information.

Referring back to FIG. 4, the pattern formation information computation unit 75 computes confidence information of repetitive pattern formation in a subroutine 105.

Figure 7:
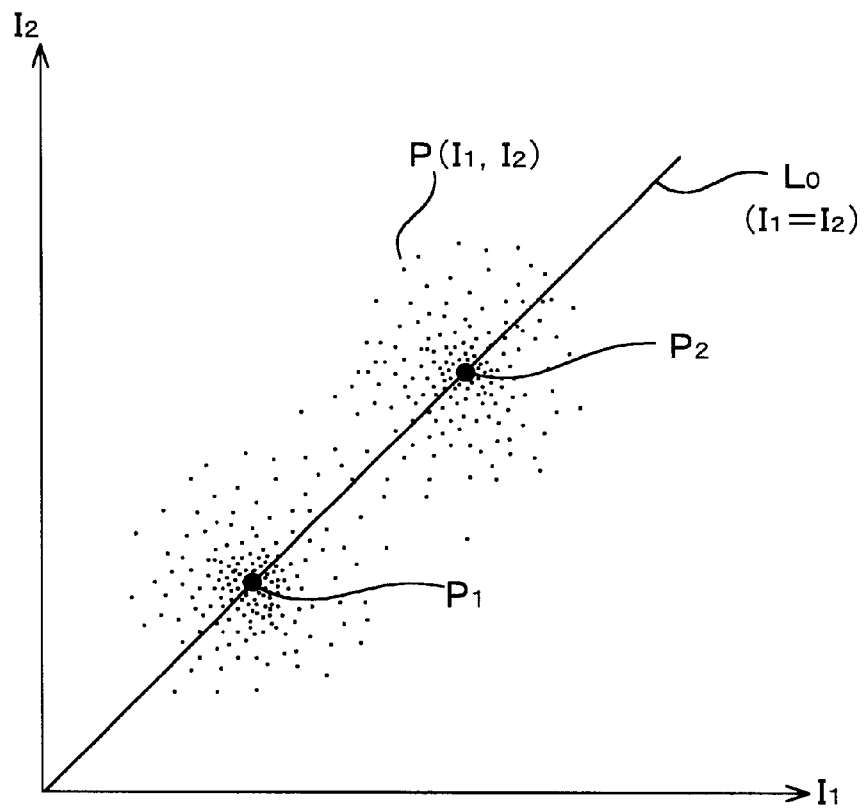
FIG. 7 is a graph showing data points plotted in a grayscale space.
Figure 8:
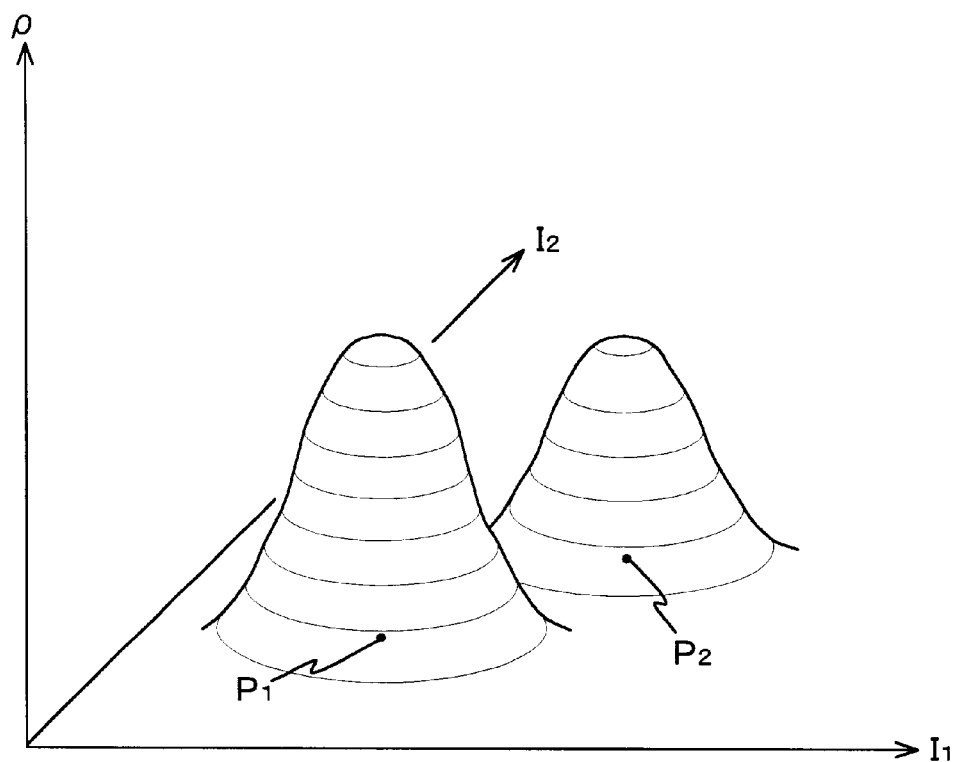
FIG. 8 is a graph showing the occurrence frequencies in the grayscale space.

Upon computing the confidence information, in step 121 in FIG. 6, the reference frequency arithmetic unit 76 reads out raw image data $I_1(X, Y)$ and shift image data $I_2(X, Y)$ from the image shift information storage area 83, and generates a data point $P(I_1, I_2)$ by combining the raw image data $I_1(X, Y)$ and shift image data $I_2(X, Y)$ at an identical X-Y coordinate position (X, Y) ($X_L+D \leq X \leq X_U$, $Y_L \leq Y \leq Y_U$). The unit 76 plots all data points $P(I_1, I_2)$ in an $I_1I_2$ coordinate space (grayscale space). FIG. 7 shows an example of the allocation result. In this embodiment, since the unit patterns are respectively formed in the unit pattern regions $91_m$ under substantially the same conditions, and are picked up under substantially the same conditions, an expectation data point $P_1$ of a space pattern portion and an expectation data point $P_2$ of a line pattern portion are plotted on a straight line $L_0$ ($I_1=I_2$) as a reference line, as shown in FIG. 7. That is, the reference line $L_0$ serves as an expectation line. Data points are distributed to have the expectation data points $P_1$ and $P_2$ as centers. FIG. 8 shows the density of data points P in the $I_1I_2$ coordinate space, i.e., the distribution of the occurrence frequency $\rho(I_1, I_2)$.

Figure 9:
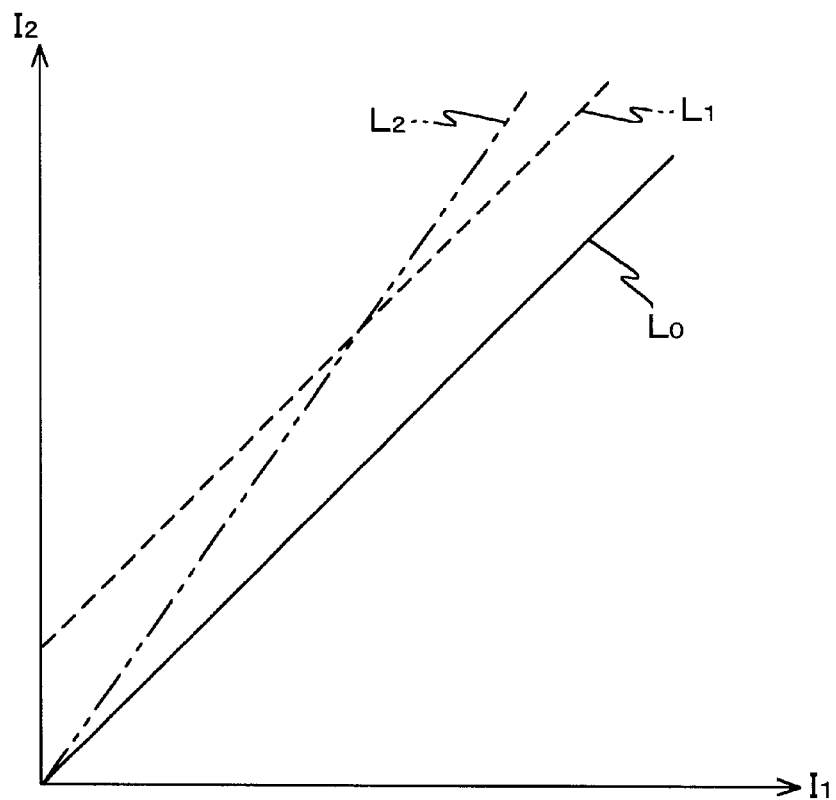
FIG. 9 shows examples of expectation curves in the grayscale space.

When unit patterns are not formed on the unit pattern regions $91_m$ under substantially the same conditions or are not picked up under substantially the same condition, e.g., when illumination light upon image pick-up does not have uniform distribution, the expectation line becomes a line $L_1$ or $L_2$ which is different from the reference line $L_0$, as shown in FIG. 9. The expectation line may become a curve in place of a straight line. However, data points are distributed around the expectation data point.

Referring back to FIG. 6, in step 122 the reference frequency arithmetic unit 76 estimates a second-order joint probability density function that pertains to probability events of occurrence of a data point P while assuming that generation of a data point $P(I_1, I_2)$ results from simultaneous generation of probability events $I_1$ and $I_2$. Upon estimation, in this embodiment, since an error of each data point P from the expectation data point occurs contingently or by chance, as described above, the reference frequency arithmetic unit 76 estimates a second-order joint probability density function as a two-dimensional normal distribution type probability density function.

The second-order joint probability density function of all the data points is a weighted sum of two-dimensional normal distribution type probability density functions having each expectation data point as an average value. Each expectation data point is located nearly on the reference line $L_0$.

The reference frequency arithmetic unit 76 divides the $I_1I_2$ coordinate space into two spaces by a straight line having an $I_1$ coordinate=t of an intersection with the reference line $L_0$ (such space division will be referred to as "division t" hereinafter), and estimates two-dimensional normal distribution type probability density functions $F_1(I_1, I_2; t)$ and $F_2(I_1, I_2; t)$ from the distributions of data points belonging to these divided spaces by:

$$F_1(I_1, I_2; t) = \exp\left[-\left\{\frac{(I_1 - \mu_{11}(t))^2}{2(\sigma_{11}(t))^2} + \frac{(I_2 - \mu_{12}(t))^2}{2(\sigma_{12}(t))^2}\right\}\right] / (2\pi \cdot \sigma_{11}(t) \cdot \sigma_{12}(t)) \quad (2)$$

$$F_2(I_1, I_2; t) = \exp\left[-\left\{\frac{(I_1 - \mu_{21}(t))^2}{2(\sigma_{21}(t))^2} + \frac{(I_2 - \mu_{22}(t))^2}{2(\sigma_{22}(t))^2}\right\}\right] / (2\pi \cdot \sigma_{21}(t) \cdot \sigma_{22}(t)) \quad (3)$$

where $\mu_{11}(t)$ and $\mu_{21}(t)$ are the average values of $I_1$ values of data points in each space divided by division t, $\mu_{12}(t)$ and $\mu_{22}(t)$ are the average values of $I_2$ values of data points in each space divided by division t, $\sigma_{11}(t)$ and $\sigma_{21}(t)$ are the standard deviations of $I_1$ values of data points in each space divided by division t, and $\sigma_{12}(t)$ and $\sigma_{22}(t)$ are the standard deviations of $I_2$ values of data points in each space divided by division t. Note that the numbers of data points in the spaces divided by division t are $Q_1(t)$ and $Q_2(t)$ (=$Q_0-Q_1(t)$).

The reference frequency arithmetic unit 76 computes a total confusion S(t) as a sum of confusions $S_1$ and $S_2$ in the spaces divided by division t using the estimated probability density functions $F_1(I_1, I_2; t)$ and $F_2(I_1, I_2; t)$ by:

$$S(t) = S_1(t) + S_2(t) \quad (4)$$

$$= -W_1(t) \cdot \int_{-\infty}^{\infty}\int_{-\infty}^{\infty} F_1(I_1, I_2; t) ln[F_1(I_1, I_2; t)] dI_1 dI_2 -$$

$$W_2(t) \cdot \int_{-\infty}^{\infty}\int_{-\infty}^{\infty} F_2(I_1, I_2; t) ln[F_2(I_1, I_2; t)] dI_1 dI_2$$

where weights $W_1(t)$ and $W_2(t)$ are respectively given by:

$$W_1(t) = Q_1(t)/(Q_1(t) + Q_2(t)) \quad (5)$$
$$= Q_1(t)/Q_0$$

$$W_2(t) = Q_2(t)/(Q_1(t) + Q_2(t)) \quad (6)$$
$$= Q_2(t)/Q_0$$

The reference frequency arithmetic unit 76 computes total confusions S(t) for individual t values while executing division t by changing the t value as a parameter. Then, the unit 76 obtains a t value $t_0$ that minimizes the total confusion S(t). The unit 76 computes two-dimensional normal distribution type probability density functions $F_1(I_1, I_2; t_0)$ and $F_2(I_1, I_2; t_0)$ that pertain to spaces divided by division $t_0$ as optimal 2-division of the space. Subsequently the reference frequency arithmetic unit 76 checks if there is another optimal division is found while further dividing each of the spaces divided by division $t_0$ in the same way as when divided by division t. As a result of the checking, in this embodiment, assume that 2-division by division $t_0$ is optimal.

The reference frequency arithmetic unit 76 computes a second-order joint probability density function $F(I_1, I_2)$ of all the data points using the probability density functions $F_1(I_1, I_2; t_0)$ and $F_2(I_1, I_2; t_0)$:

$$F(I_1, I_2) = W_1(t) \cdot F_1(I_1, I_2; t_0) + W_2(t) \cdot F_2(I_1, I_2; t_0) \qquad (7)$$

In step 123, the reference frequency arithmetic unit 76 computes an expected occurrence frequency distribution $G(I_1, I_2)$ at each coordinate position $(I_1, I_2)$ on the basis of the second-order joint probability density function $F(I_1, I_2)$ by:

$$G(I_1, I_2) = Q_0 \cdot F(I_1, I_2) \qquad (8)$$

Figure 10A:
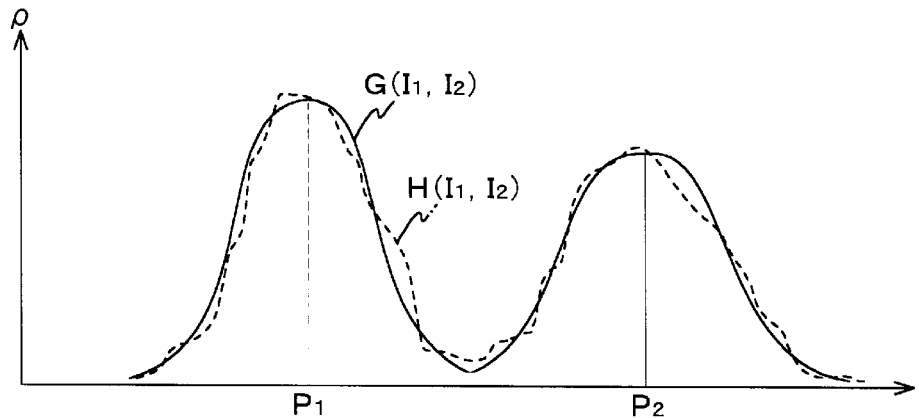
FIGS. 10A to 10C are graphs showing estimated occurrence frequency distributions.
Figure 10B:
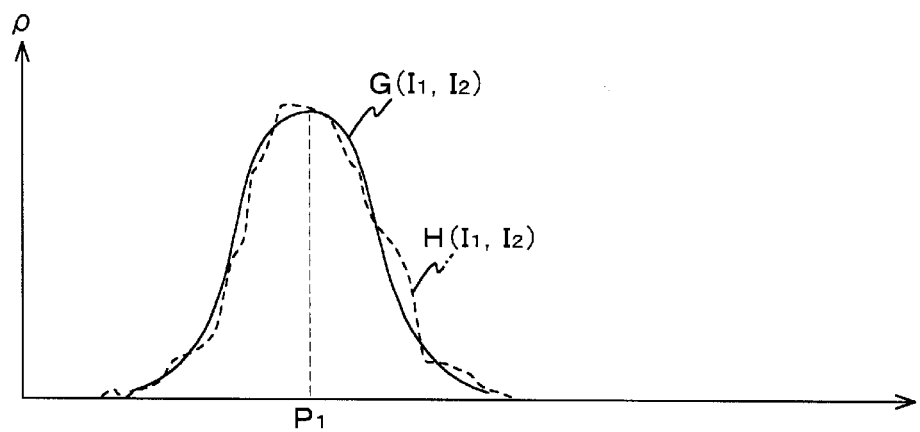
Figure 10C:
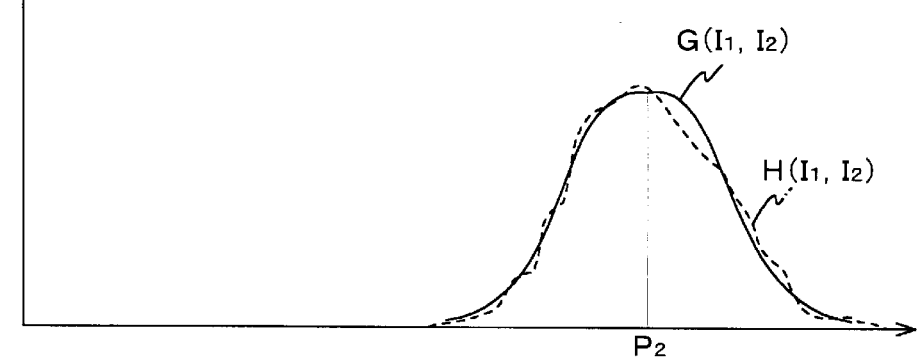
Figure 11:
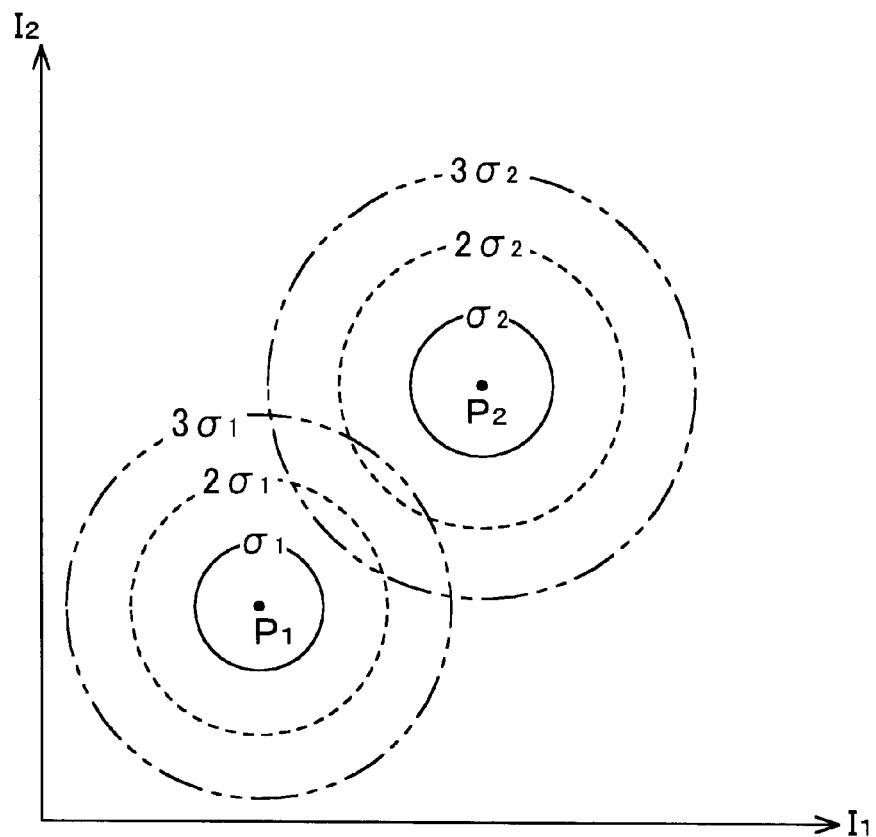
FIG. 11 is a graph showing spreads of the estimated occurrence frequency distributions in the grayscale space.

FIGS. 10A to 10C show the computed expected occurrence frequency distributions $G(I_1, I_2)$ indicated by the solid curves. FIG. 10A shows the expected occurrence frequency distribution $G(I_1, I_2)$ along the reference line $L_0$. FIG. 10B shows the expected occurrence frequency distribution $G(I_1, I_2)$ along a straight line which passes through the expectation data point $P_1(\mu_{11}, \mu_{12}(=\mu_{11}))$ and is perpendicular to the reference line $L_0$. FIG. 10C shows the expected occurrence frequency distribution $G(I_1, I_2)$ along a straight line which passes through the expectation data point $P_2(\mu_{21}, \mu_{22}(=\mu_{21}))$ and is perpendicular to the reference line $L_0$. Note that FIGS. 10A to 10C also show actual frequencies $H(I_1, I_2)$ of occurrence. In FIG. 11, a locus of 1× positions of the standard deviations is indicated by the solid curve, a locus of 2× positions of the standard deviations is indicated by the dotted curve, and a locus of 3× positions of the standard deviations is indicated by the two-dashed chain curve in association with spreads from the expectation data points $P_1$ and $P_2$ in the expected occurrence frequency distribution $G(I_1, I_2)$.

Figure 12A:
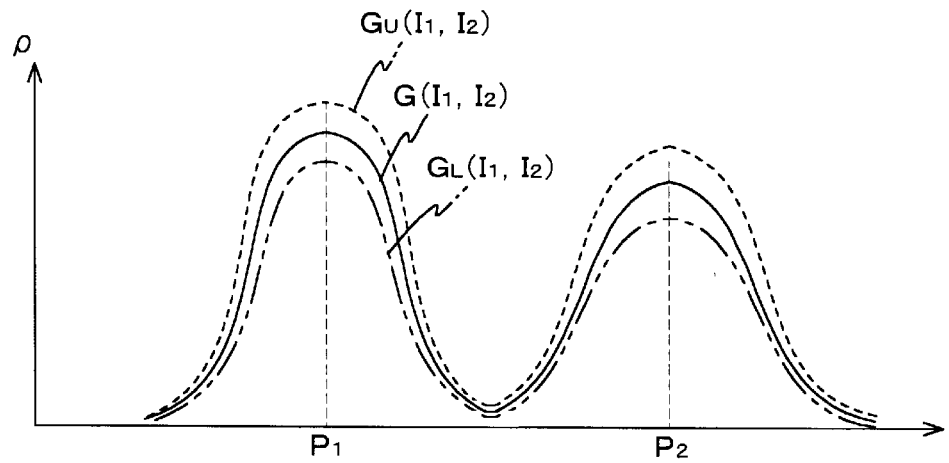
FIGS. 12A to 12C are graphs showing the confidence intervals of the estimated occurrence frequency distributions.
Figure 12B:
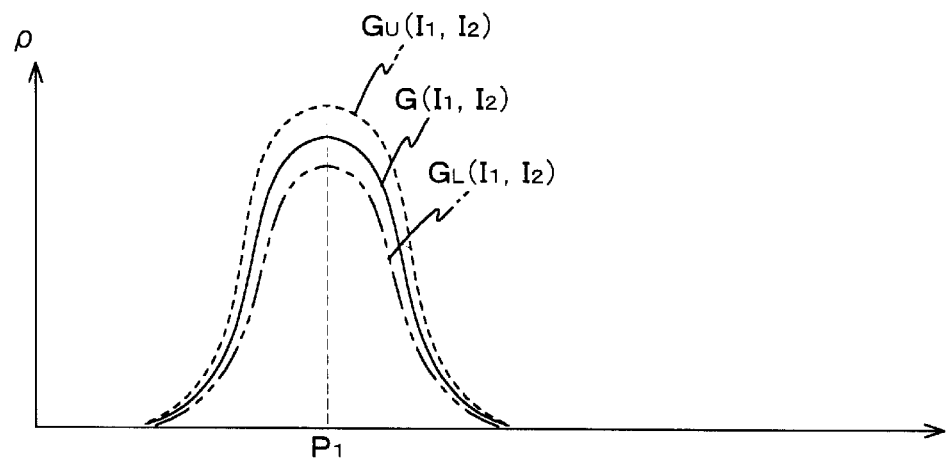
Figure 12C:
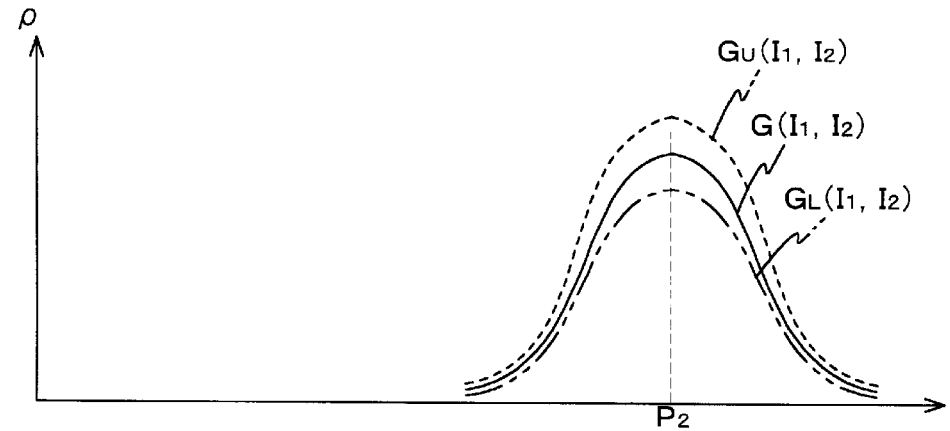

Referring back to FIG. 6, in step 124 the reference frequency arithmetic unit 76 computes the confidence interval of the expected occurrence frequency $G(I_1, I_2)$ at each coordinate position $(I_1, I_2)$ on the basis of the expected occurrence frequency distribution $G(_1, I_2)$. Upon computing the confidence interval, the reference frequency arithmetic unit 76 computes the confidence interval as an interval of the occurrence frequencies which are not contradictory to the expected occurrence frequency $G(I_1, I_2)$ at each coordinate position $(I_1, I_2)$ at a predetermined confidence (e.g., 70%) assuming that a probability distribution from which the expected occurrence frequency $G(I_1, I_2)$ at each coordinate position $(I_1, I_2)$ is obtained is a Poisson distribution. It is rational to assume a Poisson distribution since the total number $Q_0$ of data points is very large. FIGS. 12A to 12C show upper and lower limit distributions $G_u(I_1, I_2)$ and $G_L(I_1, I_2)$ of the computed confidence interval in correspondence with FIGS. 10A to 10C.

Note that it is rational to assume a binomial distribution if the total number $Q_0$ of data points is not very large.

The reference frequency arithmetic unit 76 stores the upper and lower limit distributions $G_u(I_1, I_2)$ and $G_L(I_1, I_2)$ of the confidence interval in the reference occurrence frequency storage area 84 as reference occurrence frequency information. The reference frequency arithmetic unit 76 also stores an actual occurrence frequency distribution $H(I_1, I_2)$ used to compute the aforementioned expected occurrence frequency distribution $G(I_1, I_2)$ in the reference occurrence frequency storage area 84.

Referring back to FIG. 6, in step 125 the pattern formation information arithmetic unit 77 reads out the upper and lower limit distributions $G_u(I_1, I_2)$ and $G_L(I_1, I_2)$ of the confidence interval and the actual occurrence frequency distribution $H(I_1, I_2)$ from the reference occurrence frequency storage area 84. The unit 77 compares the upper limit $G_U(I_1, I_2)$ of the confidence interval with the actual occurrence frequency distribution $H(I_1, I_2)$ at each coordinate position $(I_1, I_2)$, and also compares the lower limit $G_L(I_1, I_2)$ of the confidence interval with the actual occurrence frequency distribution $H(I_1, I_2)$.

As a result of comparison, if $$G_L(I_1, I_2) \leq H(I_1, I_2) \leq G_U(I_1, I_2) \qquad (9)$$

the pattern formation information arithmetic unit 77 evaluates that no pattern defects are present at those positions on the surface of the wafer W, which correspond to data points at that coordinate position $(I_1, I_2)$.

On the other hand, if $$G_U(I_1, I_2) > H(I_1, I_2) \qquad (10)$$

the pattern formation information arithmetic unit 77 evaluates that pattern defects are unlikely to be present at those positions on the surface of the wafer W, which correspond to data points at that coordinate position $(I_1, I_2)$, but pattern defects are highly likely to be present at those positions on the surface of the wafer W, which correspond to data points at a coordinate position elsewhere.

If $$G_U(I_1, I_2) < H(I_1, I_2) \qquad (11)$$

the pattern formation information arithmetic unit 77 evaluates that pattern defects are highly likely to be present at those positions on the surface of the wafer W, which correspond to some of data points of that coordinate position $(I_1, I_2)$. Such data point will be referred to as a "defect candidate data point" hereinafter. A probability $FP(I_1, I_2)$ that pattern defects are respectively present at those positions on the surface of the wafer W, which correspond to data points of that coordinate position $(I_1, I_2)$ is evaluated to be:

$$FP(I_1, I_2) = (H(I_1, I_2) - G_U(I_1, I_2)) / H(I_1, I_2) \qquad (12)$$

For example, if the upper limit $G_U(I_1, I_2)$ of the confidence interval is 3.2 and the actual frequency $H(I_1, I_2)$ of occurrence is 4 in association with a given coordinate position $(I_1, I_2)$, it is evaluated that pattern defects are present at positions on the surface of the wafer W corresponding to four data points that account for the actual occurrence frequency $H(I_1, I_2)$ at a probability of 0.2 (=(4−3.2)/4), and no pattern defects are present at these positions at a probability of 0.8 (=1−0.2).

The pattern formation information arithmetic unit 77 makes the aforementioned evaluation for the individual coordinate positions $(I_1, I_2)$, and stores the evaluation results as pattern formation information, i.e., confidence information that pertains to pattern formation, in the pattern formation information storage area 85.

In this way, the process of the subroutine 105 ends, and the flow returns to the main routine.

Referring back to FIG. 4, in step 107 the defect position arithmetic unit 78 reads out the confidence information that pertains to pattern formation from the pattern formation information storage area 85, and obtains candidate positions where pattern defects are present on the surface of the wafer W. Upon obtaining candidate positions where pattern defects are likely to be present on the surface of the wafer W, the defect position arithmetic unit 78 obtains X-Y coordinate positions corresponding to defect candidate data points in the confidence information. When a given X-Y coordinate position (X, Y) corresponds to a defect candidate data point, the defect position arithmetic unit 78 checks if an X-Y coordinate position (X−D, Y) or (X+D, Y) is present as that corresponding to another defect candidate data point. The reason why such checking is made is that (1) whether defect candidate data resulted from the raw image (i.e., the $I_1$, value) or the shift image (i.e., the $I_2$ value) cannot be determined, and (2) the signal level at the X-Y coordinate position (X, Y) of the raw image is also that at the X-Y coordinate position (X+D, Y) of the shift image, and the signal level at the X-Y coordinate position (X, Y) of the shift image is also that at the X-Y coordinate position (X−D, Y) of the raw image, as described above.

As a result, if neither the X-Y coordinate position (X−D, Y) nor the X-Y coordinate position (X+D, Y) are present as the X-Y coordinate position corresponding to another defect candidate data point, and $(X_L+2D) \leq X \leq (X_U-D)$, the defect position arithmetic unit 78 determines that no pattern defects are present at that X-Y coordinate position (X, Y). On the other hand, if $X<(X_L+2D)$, the defect position arithmetic unit 78 extracts the X-Y coordinate position (X−D, Y) of the raw image as a defect candidate position; if $X>(X_U-D)$, it extracts the X-Y coordinate position (X, Y) of the raw image as a defect candidate position.

On the other hand, if only the X-Y coordinate position (X−D, Y) is present as that corresponding to another defect candidate data point, the defect position arithmetic unit 78 extracts the X-Y coordinate position (X−D, Y) of the raw image as a defect candidate position. On the other hand, if only the X-Y coordinate position (X+D, Y) is present as that corresponding to another defect candidate data point, the defect position arithmetic unit 78 extracts the X-Y coordinate position (X, Y) of the raw image as a defect candidate position.

Furthermore, if both the X-Y coordinate positions (X−D, Y) and (X+D, Y) are present as those corresponding to other defect data candidate data points, the defect position arithmetic unit 78 extracts the X-Y coordinate positions (X−D, Y) and (X, Y) of the raw image as defect candidate positions.

The defect position arithmetic unit 78 stores the extracted defect candidate positions in the defect candidate position information storage area 86 as defect candidate position information.

In step 108, the control unit 79 reads out the defect candidate position information from the defect candidate position information storage area 86, and outputs it as inspection result data to the display unit 62, which displays the defect candidate positions on the surface of the wafer W as inspection results. To allow the operator to recognize the defect candidate positions on the surface of the wafer W upon displaying them, it is preferable to read out picked-up image data from the picked-up image data storage area 81 by the control unit 79, convert the X-Y positions of the defect candidate positions into those on the coordinate system of the picked-up image data, and superimpose the raw image and defect candidate positions on the display.

The operator checks by observing the inspection results displayed on the display unit 62 if pattern defects are actually present at the defect candidate positions. Note that the operator inputs control data from the input unit 63 as needed to observe a portion around the defect candidate position via the image pick-up unit 20, and specifies the position on the surface of the wafer W where the defects are present. In this manner, inspection of the formation state of repetitive patterns on the wafer W is completed.

In step 109, the controller 55 unloads the wafer W from the sample chamber 22 using the arm 53 in procedures opposite to loading of the wafer W in step 101, and stores that wafer W in the cassette 59.

The control unit 79 checks in step 110 if the next wafer to be inspected is present. In this case, YES is determined since only one wafer W has been inspected, and the flow advances to step 111.

In step 111, the next wafer is loaded on the X-Y stage 45 of the image pick-up unit 20 in the same manner as in step 101 described above. After that, steps 102 to 109 are executed to inspect each wafer until NO is determined in step 110. Then, when NO in step 110, and inspection is complete for all the wafers to be inspected, the inspection process ends.

As described above, according to this embodiment, on the basis of a multi-gray level raw image obtained by picking-up the surface of the wafer W, and a shift image obtained by shifting the raw image in the repetition direction by the repetition period of patterns, sets of gray levels of the raw and shift images at identical X-Y positions are defined as data points in a two-dimensional coordinate space ($I_1 I_2$ coordinate space), data points corresponding to positions of the overlapping region of the raw and shift image are plotted in the $I_1 I_2$ coordinate space, and the distribution state of the data points in the $I_1 I_2$ coordinate space are statistically analyzed as a probably distribution, thus obtaining pattern formation information that pertains to pattern defects on the surface of the wafer W. Hence, pattern defects can be accurately found by inspection while fully reflecting multi-gray level information at respective points of the multi-gray level image.

Since the repetition direction and period of the image pick-up result are obtained by analyzing the raw image, those on the surface of the wafer W loaded into the inspection apparatus can be precisely specified, and pattern defects can be accurately inspected.

Upon obtaining the pattern formation information on the surface of the wafer W from the distribution state of data points in the $I_1 I_2$ coordinate space, the second-order joint probability density function is estimated from the distribution of data points in the $I_1 I_2$ coordinate space, the relationship between the reference and actual occurrence frequencies at each coordinate position of the $I_1 I_2$ coordinate space is computed, and pattern formation information that pertains to pattern defects of an object is obtained on the basis of the relationship between the reference and actual occurrence frequencies, thus accurately obtaining statistically appropriate pattern formation information.

The reference occurrence frequency is used as the upper and lower limit values of the confidence interval corresponding to a predetermined statistical confidence which pertains to an expectation value of the occurrence frequency at each coordinate position of the $I_1 I_2$ coordinate space, and the presence/absence of pattern defects is estimated by comparing the reference and actual occurrence frequencies. Hence, statistically appropriate pattern formation information can be accurately obtained.

Since the second-order joint probability density function is estimated as a mixture of a plurality of two-dimensional normal distribution type probability density functions, statistically appropriate pattern formation information can be accurately obtained. If probability density functions of errors of data points are known, they can be used.

The second-order joint probability density function is estimated by breaking up the $I_1I_2$ coordinate space into a plurality of partial spaces by a straight line perpendicular to the reference line as a set of points having equal coordinate values in the $I_1I_2$ coordinate space, estimating two-dimensional normal distribution type probability density functions in units of partial spaces from the data points in these partial spaces, and computing the sum of the two-dimensional normal distribution type probability density functions in units of partial spaces by weighting them depending on the corresponding numbers of data points. Therefore, a statistically appropriate second-order joint probability density function can be estimated while reducing the computation volume.

Since the second-order joint probability density function is obtained by dividing the $I_1I_2$ coordinate space into a plurality of partial spaces using division that minimizes the overall confusion as optimal space division, a statistically maximally likely second-order joint probability density function can be obtained.

In the above embodiment, the presence/absence of pattern defects is determined based on the relationship between the reference and actual occurrence frequencies using the upper and lower limit values of the confidence interval that pertains to expectation values of the occurrence frequencies at respective coordinate positions in the $I_1I_2$ coordinate space, when the estimated second-order joint probability density function is used. Alternatively, the expectation values of the occurrence frequencies may be used as reference occurrence frequencies, and the presence/absence of pattern defects may be determined based on the ratio between the reference and actual occurrence frequencies. Even in such case, statistically appropriate pattern formation information can be obtained.

In the above embodiment, upon estimating the second-order joint probability density function, the coordinate space is divided to minimize the total randomness of the data point distribution, two-dimensional normal distribution type probability density functions are estimated in units of divided spaces (partial spaces), and the sum of the weighted two-dimensional normal distribution type probability density functions is computed. Alternatively, other statistical maximum likelihood methods may be used.

Figure 13A:
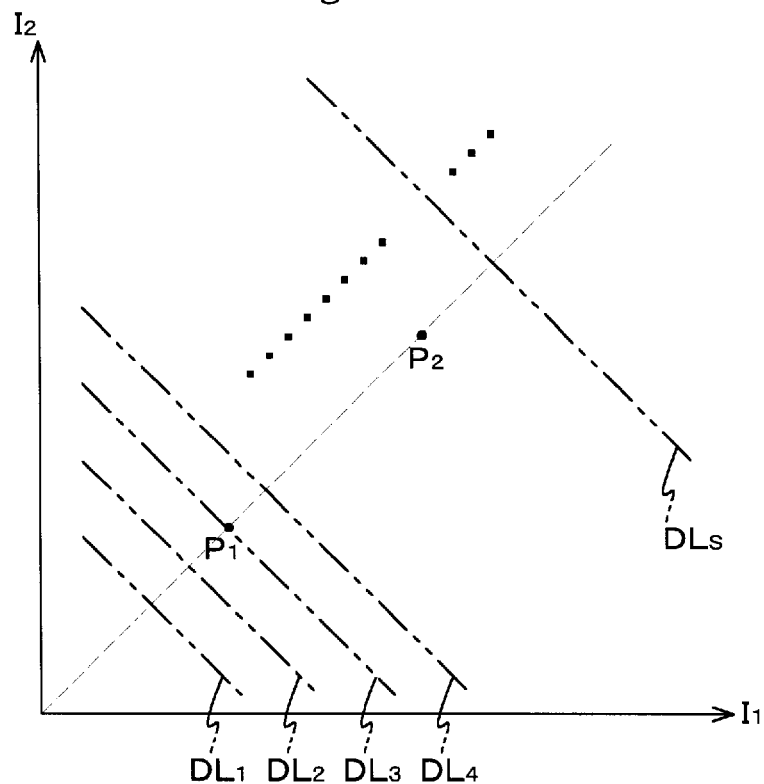
FIGS. 13A and 13B are graphs (part 1) for explaining a modification of the first embodiment.
Figure 13B:
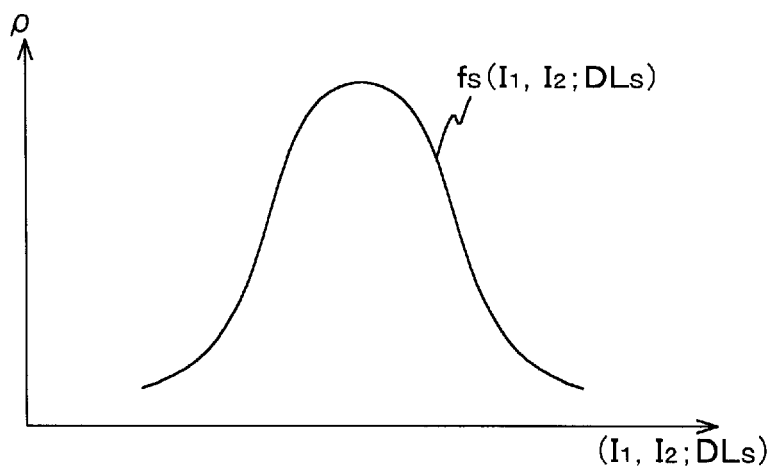

The second-order joint probability density function of all the data points may be estimated by (1) dividing the $I_1I_2$ coordinate space into a plurality of partial spaces using a plurality of lines $DL_S$ (S=1, 2, . . . ) which are perpendicular to the reference line, as shown in FIG. 13A, (2) mapping data points in the plurality of partial spaces onto the corresponding lines $DL_S$, (3) computing one-dimensional normal distribution type probability density functions $f_S(I_1, I_2; DL_S)$ shown in FIG. 13B of the plurality of partial spaces on the basis of the one-dimensional distribution of the mapped data points, and (4) weighting the one-dimensional normal distribution type probability density functions $f_S(I_1, I_2; DL_S)$ depending on the numbers of data points in units of partial spaces. Note that $(I_1, I_2; DL_S)$ indicates that variables are $I_1$ and $I_2$ values on the line $DL_S$. In such case, the second-order joint probability density function can be estimated while maintaining high accuracy to some extent, and reducing the computation volume.

Figure 14A:
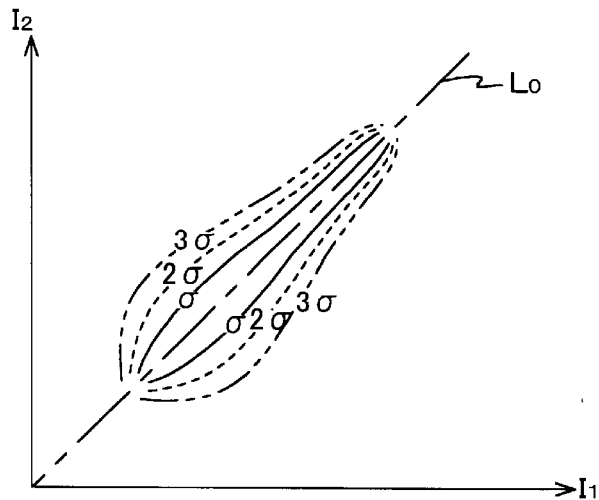
FIGS. 14A to 14C are graphs (part 2) for explaining a modification of the first embodiment.
Figure 14B:
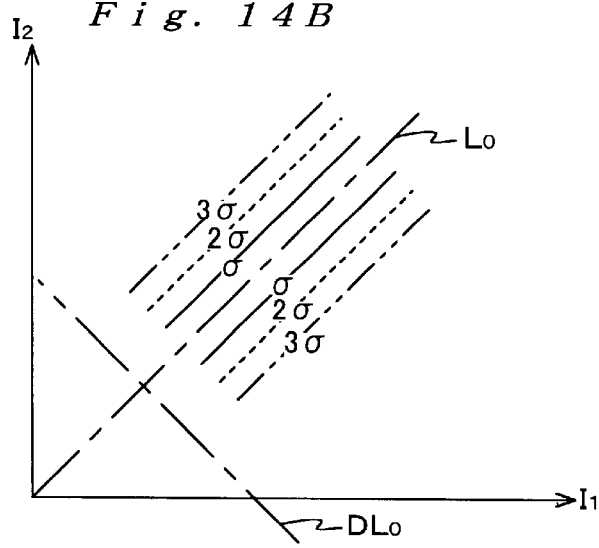
Figure 14C:
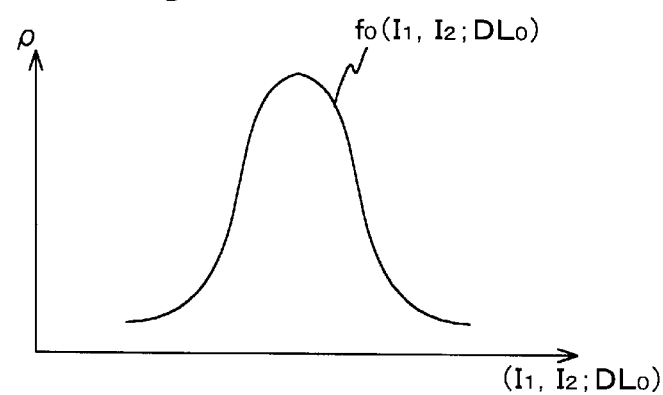
Figure 15:
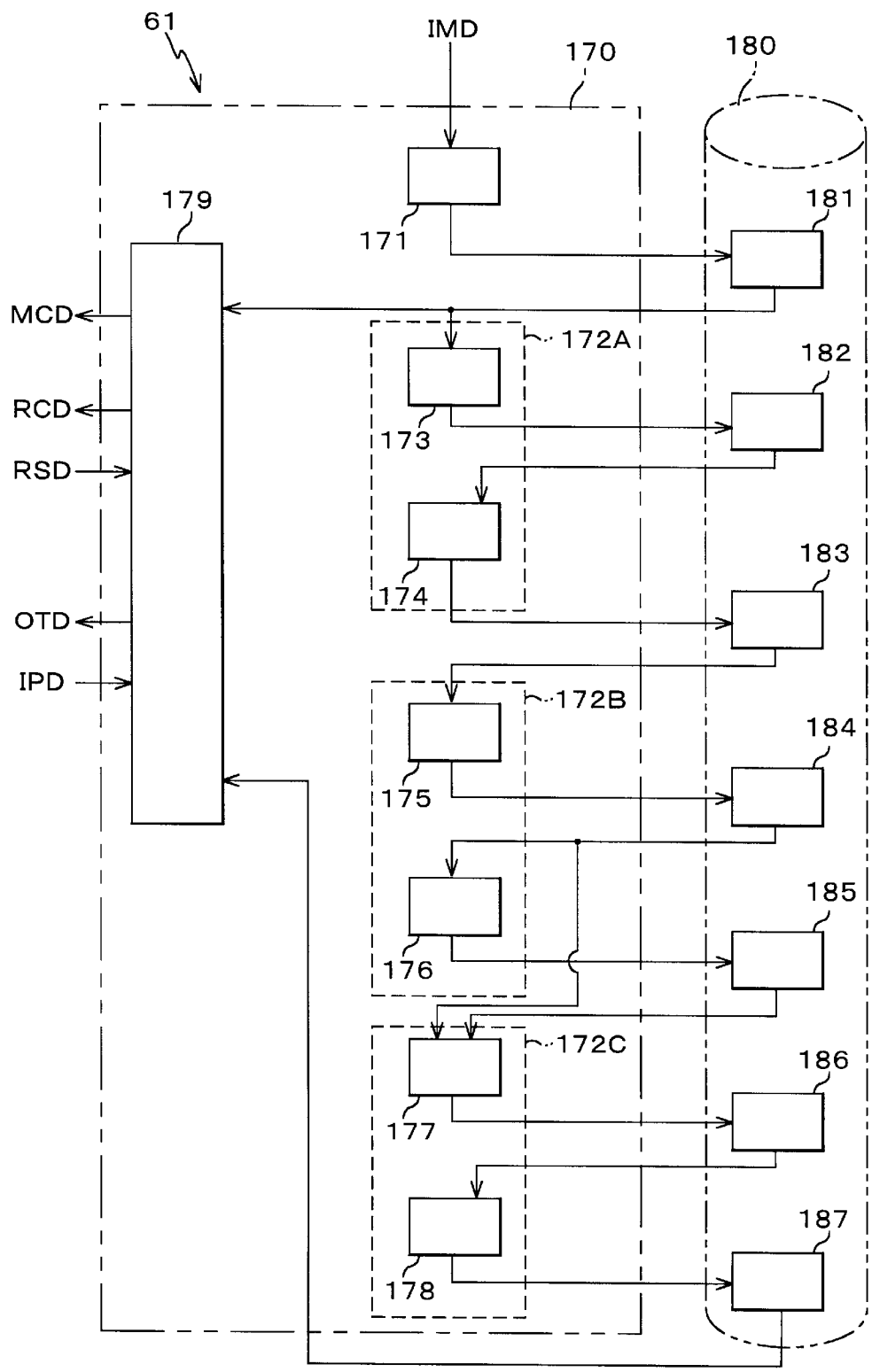
FIG. 15 is a diagram showing the arrangement of a processing control system in the second embodiment.

When the second-order joint probability density function is obtained using the one-dimensional normal distribution type probability density functions $f_S(I_1, I_2; DL_S)$, as described above, lines that connect 1×, 2×, and 3× positions of the standard deviations of the respective one-dimensional normal distribution type probability density functions $f_S(I_1, I_2; DL_S)$ normally become curves, as indicated by lines σ, 2σ, and 3σ shown in FIG. 14A. If the lines σ, 2σ, and 3σ are nearly parallel to the reference line $L_0$, as shown in FIG. 14B, all data points are mapped on a straight line $DL_0$ perpendicular to the reference line $L_0$, and a one-dimensional normal distribution type probability function $f_0(I_1, I_2; DL_0)$ (FIG. 14C) is computed from the one-dimensional distribution of the mapped data points and can be used as a joint probability density function. In such case, since the computation volume can be greatly reduced while maintaining high estimation accuracy of the joint probability density function of all the data points, the formation state of repetitive patterns on the object can be inspected very quickly while maintaining high inspection accuracy.

In the above embodiment, one shift image is used, and the grayscale space is a two-dimensional space. Alternatively, pattern formation information may be obtained using (N−1) (N is an integer equal to or larger than 3) shift images having different shift amounts may be used, and an N-dimensional space as the grayscale space.

<<Second Embodiment>>

The second embodiment of the present invention will be described below mainly with reference to FIGS. 15 to 20.

An inspection apparatus of this embodiment is substantially the same as the inspection apparatus 10 of the first embodiment mentioned above, except for the configuration and function of the processing control system 60. Such differences will be mainly explained below. Note that the same reference numerals denote the same or equivalent components as in the inspection apparatus 10 of the first embodiment, and a repetitive description thereof will be avoided.

The processing control system 60 of this embodiment comprises a processing control unit 161 which processes control data, and processes surface image data of a wafer W obtained by the image pick-up unit 20 to obtain pattern formation information that pertains to pattern defects on the wafer surface, and a display unit 62 and input unit (keyboard and the like) 63 connected to the processing control unit 161. The display unit 62 displays the image pick-up result (e.g., secondary electron image) of the image pick-up unit 20, the processing result of the image pick-up result data, and the like, and the input unit 63 allows the operator to input commands, various processing conditions, and the like to the processing control unit 161.

Figure 18:
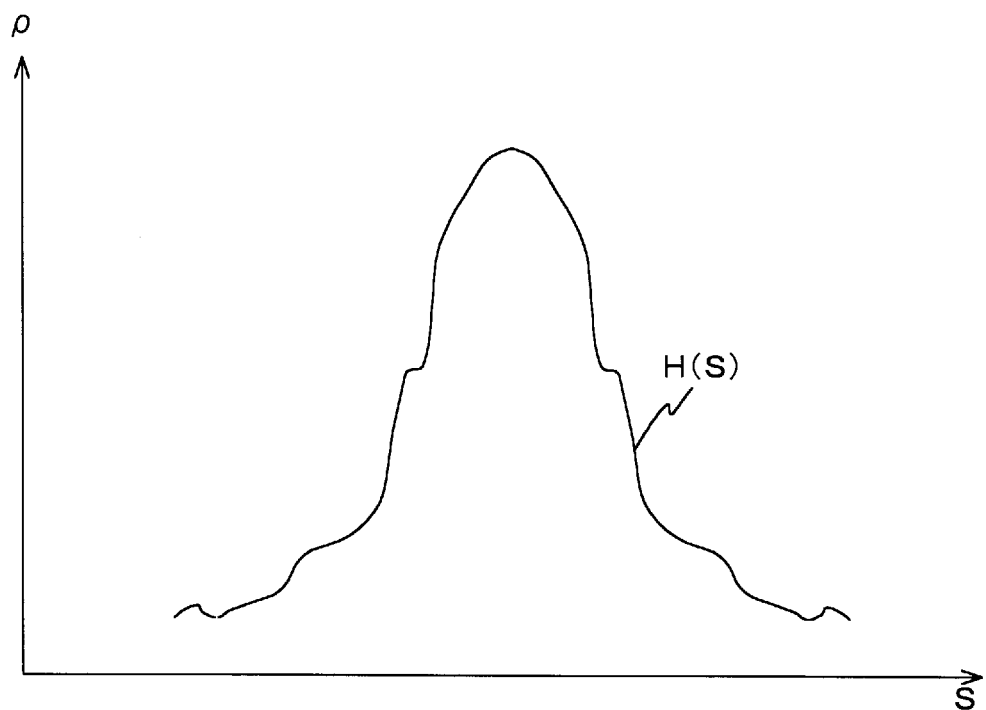
FIG. 18 is a graph showing actual occurrence frequencies of difference data.

The processing control unit 161 comprises a data processing unit 170 and storage unit 180, as shown in FIG. 18.

The data processing unit 170 comprises (a) a control unit 179 for controlling the operation of the image pick-up unit 20 by supplying, e.g., image pick-up unit control data MCD to the controller 39 of the image pick-up unit 20, and controlling the operation of the convey unit 50 by supplying, e.g., convey unit control data RCD to the controller 55 of the convey unit 50, (b) a picked-up image data acquisition unit 171 for acquiring picked-up image data IMD sent from the image pick-up unit 20, (c) an image shift unit 172A for obtaining a raw image from the acquired picked-up image data, and obtaining a shift image obtained by shifting the raw image by a repetition period in the repetition direction of patterns in the raw image, (d) a difference data classifying unit 172B for obtaining abnormal difference data candidates from the distribution of difference data of gray levels as relationship data of gray levels at identical positions in the raw image and a reference image, and (e) a discrimination unit 172C for discriminating whether or not an abnormal difference data candidate is abnormal difference data, on the basis of probability values including an abnormal probability of the abnormal difference data candidate, and that of difference data (to be referred to as "corresponding difference data" hereinafter) that pertains to the position in the shift image corresponding to the raw image position of that abnormal difference data candidate. The control unit 179 receives state information RSD that pertains to turning, vertical movement, and extensible movement of the arm 53 from the convey unit 50, and receives information IPD input by the operator from the input unit 63. Furthermore, the control unit 179 supplies output data OTD as display data to the display unit 62.

The image shift unit 172A has (i) a repetition information computation unit 173 for obtaining the repetition direction and period of patterns in the raw image by analyzing the raw image, and (ii) a shift computation unit 174 for obtaining a shift image using the repetition direction and period obtained by the repetition information computation unit 173.

The difference data classifying unit 172B has (i) an estimation unit 175 for estimating a first probability density function that pertains to the occurrence probabilities of difference data on the basis of the distribution of difference data of gray levels as relationship data of gray levels at identical positions in the raw and reference images, then estimating a second probability density function that pertains to the occurrence frequencies of individual difference data values, and obtaining a confidence interval of a predetermined confidence which pertains to the occurrence frequencies of the difference data, and (ii) an extraction unit 176 for extracting abnormal difference data candidates on the basis of the actual occurrence frequencies of the difference data, and the confidence interval.

The discrimination unit 172C has (i) a probability product computation unit 177 for computing the abnormal probability of a given extracted abnormal difference data candidate, computing the abnormal probability of corresponding difference data, and computing the product of these abnormal probabilities, and (ii) an evaluation unit 178 for evaluating appropriateness as to whether that abnormal difference data candidate is abnormal difference data by checking if the probability product is larger than a predetermined threshold value.

The operations of units that construct the processing control unit 161 will be described later.

The storage unit 180 has a picked-up image data storage area 181, a repetition information storage area 182, an image shift information storage area 183 for storing raw and shift image data, an estimated information storage area 184 for storing the difference data distribution and the estimated first and second probability density functions, an abnormal difference data candidate storage area 185 for storing abnormal difference data candidates, a probability product storage area 186 for storing probability products associated with the abnormal difference data candidates, and an abnormal data position storage area 187 for storing the position on the surface of the wafer W where abnormal difference data is generated.

In this embodiment, the processing control unit 161 is constructed by combining various units. Alternatively, the processing control unit 161 may be constructed as a computer system, and the function of the units that construct the data processing unit 170 may be implemented by a program installed in the processing control unit 161.

Inspection of a wafer W by the inspection apparatus 10 with the aforementioned arrangement will be explained below.

Assume that a plurality of (three in FIG. 1) wafers W to be inspected are stored in the cassette 59.

Also, assume that, in this embodiment, repetitive patterns are formed on a repetitive pattern region $90_1$ on the surface of the wafer W to be inspected, as shown in FIG. 3, as in the first embodiment. That is, in the repetitive pattern region $90_1$, unit pattern regions $91_1$ to $91_M$ which have the same X-width and on each of which an identical unit pattern made up of line and space patterns are formed line up in the X-direction.

In this embodiment, the unit patterns are formed on the individual unit pattern regions $91_m$ (m=1 to M) under substantially the same conditions, and are picked up under substantially the same conditions free from, e.g., any gradients of the exposure light amount and image pick-up illumination light amount in the X-Y space, as in the first embodiment.

Furthermore, assume that information as the aforementioned conditions of inspection is input by the operator to the processing control unit 161 (more specifically, control unit 179) via the input unit 63. Based on such input information, inspection of the inspection apparatus 10 of this embodiment starts under the systematic control of the processing control system 60.

The inspection process that pertains to the formation state of repetitive patterns on the surface of the wafer W will be explained below based on the flow chart shown in FIG. 16 while referring to other drawings as needed.

Figure 16:
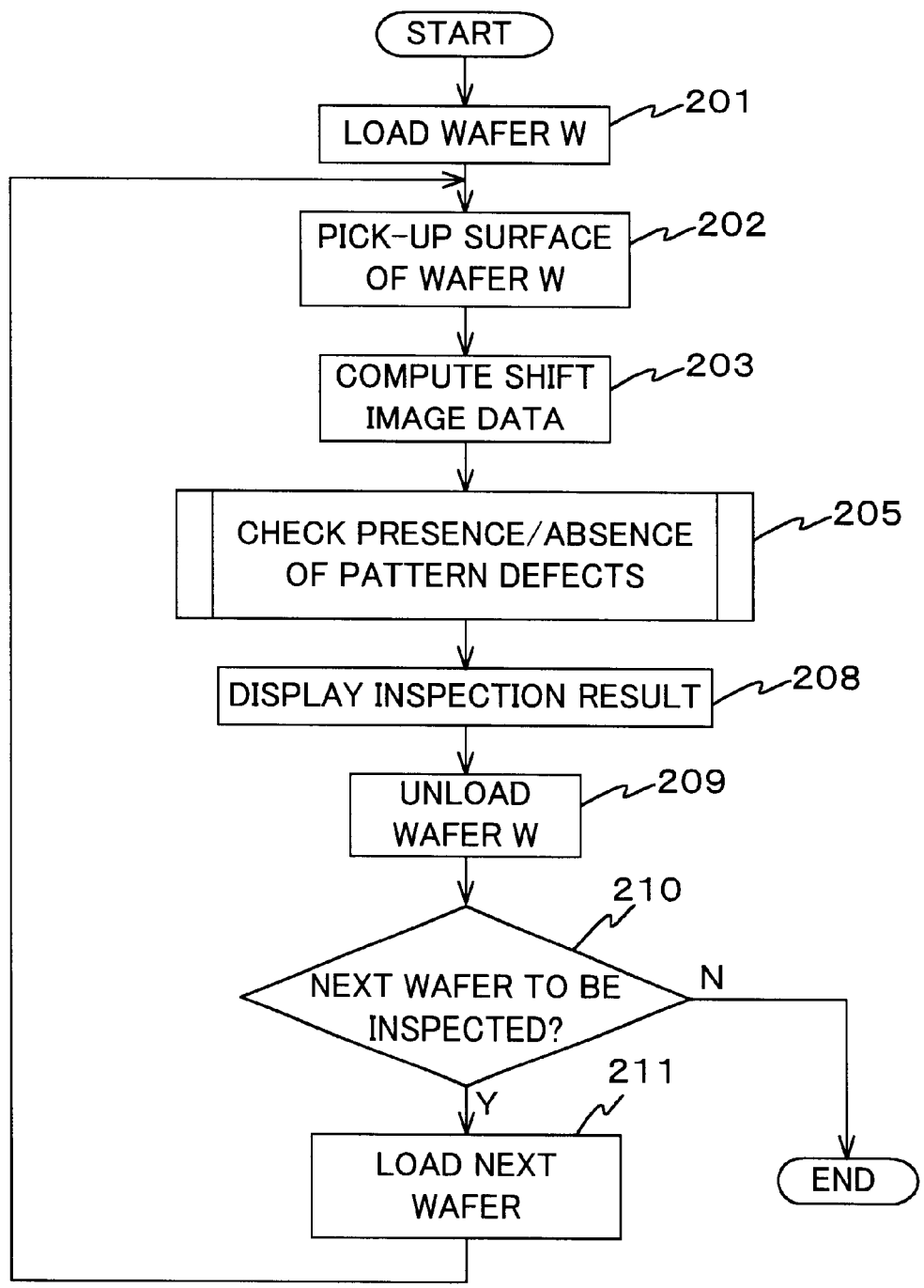
FIG. 16 is a flow chart showing the process for inspecting the formation state of repetitive patterns in the second embodiment.

In steps 201 to 203 in FIG. 16, one of the wafers W in the data cassette 59 is loaded onto the X-Y stage 45 of the image pick-up unit 20 (step 201), the image of the surface of the wafer W is picked up (step 202), and shift image data is computed, as in steps 101 to 103 in FIG. 4. Upon computing the shift image data, the repetition information computation unit 173 in the image shift unit 172A reads out raw image data from the picked-up image data storage area 181, and analyzes the raw image data to extract the aforementioned repetitive pattern region $90_1$ and to also extract as repetitive pattern information the repetition direction (X-direction in FIG. 3) and repetition period (the X-width of the unit pattern region $91_m$ in FIG. 3) of the patterns. FIG. 5A shows an example of the extracted repetitive pattern information. In this embodiment, the following explanation will be given assuming that the repetitive pattern region $90_1$ is a rectangular region defined by X-positions $X_L$ to $X_U$ and Y-positions $Y_L$ to $Y_U$, the repetition direction of the patterns agrees with the X-direction, and the repetition period is D, as shown in FIG. 5A, as in the first embodiment. The repetition information computation unit 173 stores the obtained repetitive pattern information, and image data in the repetitive pattern region $90_1$ in the repetition information storage area 182. Note that $I_1(X, Y)$ represents the gray level (to be also referred to as a "signal level" hereinafter) of each pixel in the image data in the repetitive pattern region $90_1$.

The shift computation unit 174 in the image shift unit 172A reads out the repetitive pattern information and the image data in the repetitive pattern region $90_1$ from the repetition information storage area 182, and computes shift image data by shifting the image data in the repetitive pattern region $90_1$ by the distance D in the X-direction. FIG. 5B shows the shift image obtained in this way. That is, the shift image has a repetitive pattern region $90_2$ which is a rectangular region defined by X-positions $(X_L+D)$ to $(X_U+D)$ and Y-positions $Y_L$ to $Y_U$, the pattern repetition direction which agrees with the X-direction, and the repetition period=D, as shown in FIG. 5B, as in the first embodiment. Note that $I_2(X, Y)$ represents the signal level of each pixel in the image data in the repetitive pattern region $90_2$.

The shift computation unit 174 stores raw image data $I_1(X, Y)$ and shift image data $I_2(X, Y)$ in the image shift information storage area 183 as image shift information.

Referring back to FIG. 16, the presence/absence of pattern defects on the surface of the wafer W is discriminated in a subroutine 205. Note that details of the subroutine 205 for discriminating the presence/absence of pattern defects is shown in FIG. 17.

Figure 17:
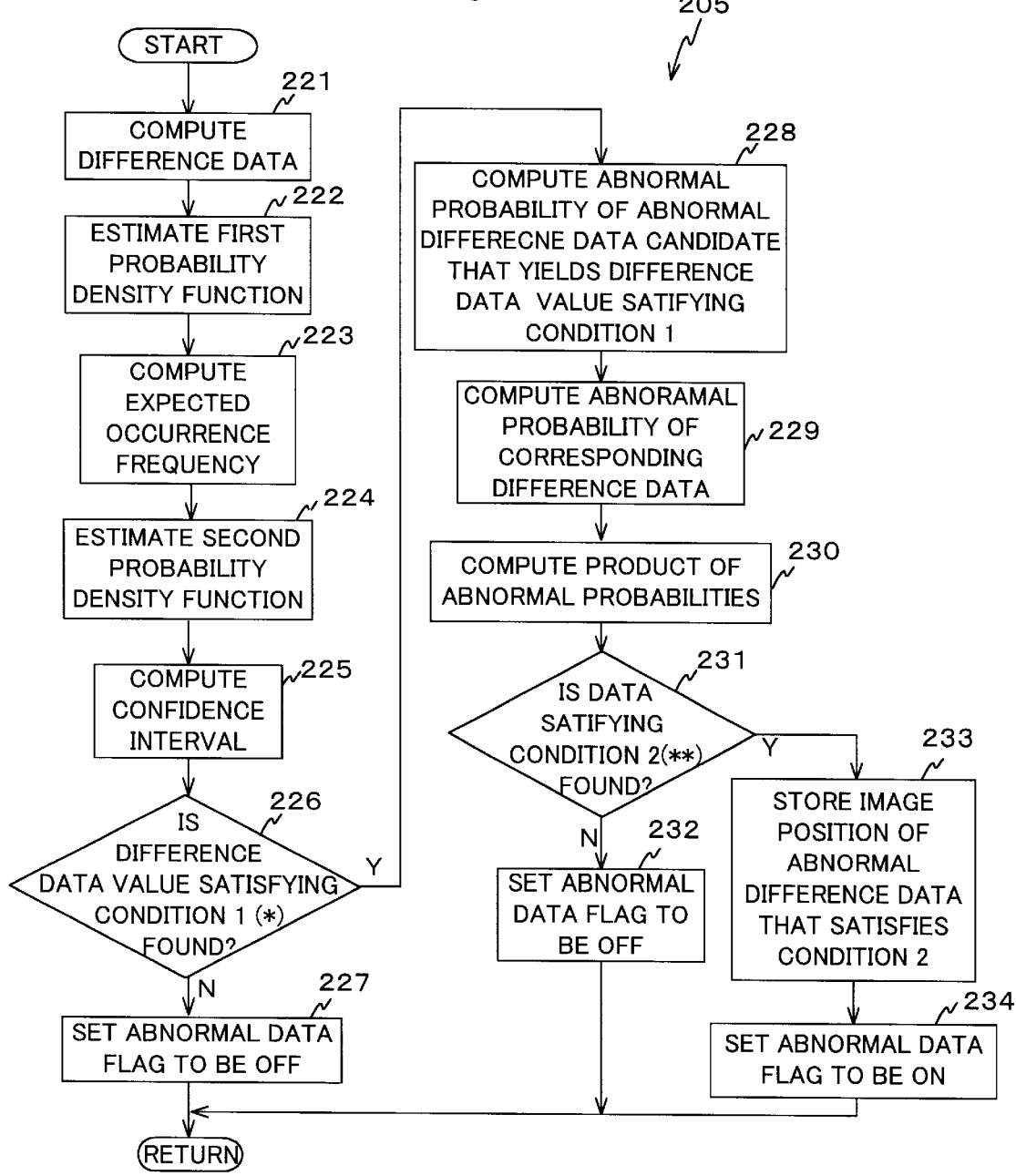
FIG. 17 is a flow chart showing the process for computing the confidence upon forming repetitive patterns in the second embodiment.

At the beginning of discrimination, in step 221 in FIG. 17 the estimation unit 175 of the difference data classifying unit 172B reads out raw image data $I_1(X, Y)$ and shift image data $I_2(X, Y)$ from the image shift information storage area 183. The estimation unit 175 computes difference data $S(X, Y)$ between the raw image data $I_1(X, Y)$ and shift image data $I_2(X, Y)$ at identical X-Y coordinate positions $(X, Y)$ $(X_L+D \leq X \leq X_U, Y_L \leq Y \leq Y_U)$ by:

$$S(X, Y) = I_1(X, Y) - I_2(X-Y) \quad (13)$$

FIG. 18 shows a distribution $\rho(S)$ of occurrence frequencies of values of the difference data $S(X, Y)$ computed in this way. In the following description, $H(S)$ represents an actual occurrence frequency distribution shown in FIG. 18.

Referring back to FIG. 17, in step 222 the estimation unit 175 hypothetically determines generation of difference data S as a probability event, and estimates a first probability density function $F(S)$ that pertains to the probability event of occurrence of the difference data S. Upon estimation, in this embodiment, since difference data S may occur contingently, as described above, the estimation unit 175 estimates the first probability density function $F(S)$ as a normal distribution type probability density function having zero average value $\mu_s$ by:

$$F(S) = \frac{1}{\sqrt{2\pi} \cdot \sigma} \exp\left[\frac{-(S-\mu_S)^2}{2\sigma^2}\right] \quad (14)$$
$$= \frac{1}{\sqrt{2\pi} \cdot \sigma} \exp\left[\frac{-S^2}{2\sigma^2}\right]$$

In step 223, the estimation unit 175 computes expected occurrence frequencies of the respective values of the difference data S, i.e., an expected occurrence frequency distribution $G(S)$ on the basis of the probability density function $F(S)$ and the number of difference data, i.e., the aforementioned value $Q_0$ by:

$$G(S) = Q_0 \cdot F(S) \quad (15)$$

Figure 19:
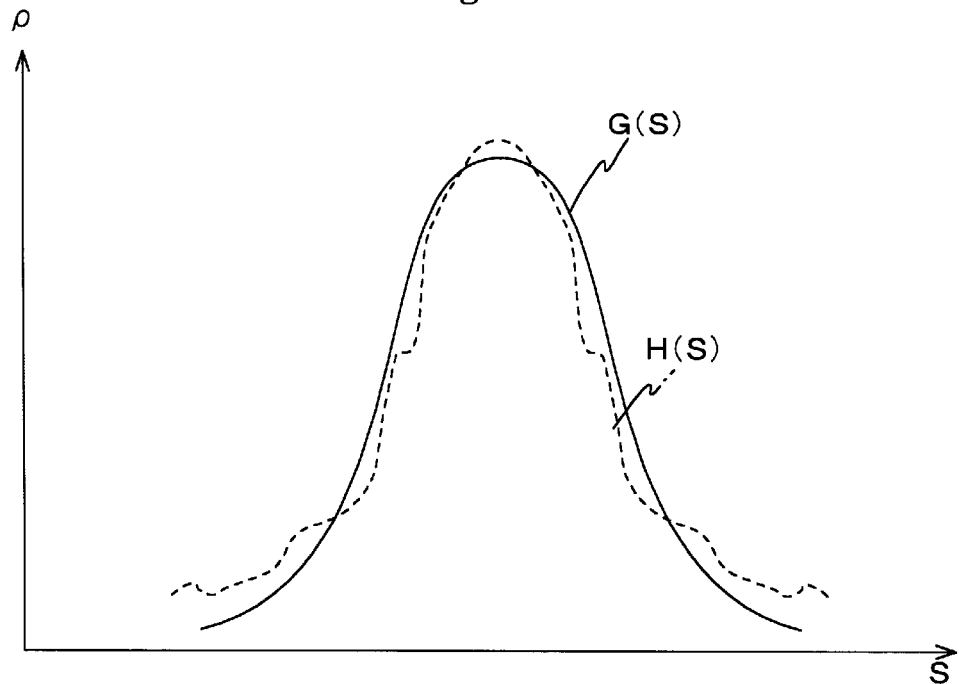
FIG. 19 is a graph showing expected occurrence frequencies of difference data.

The expected occurrence frequency distribution $G(S)$ computed in this manner is indicated by the solid curve in FIG. 19. Note that FIG. 19 also shows an actual occurrence frequency distribution $H(S)$ indicated by the dotted curve.

Referring back to FIG. 17, in step 224 the estimation unit 175 estimates a second probability density function that pertains to the occurrence frequencies of the individual values of difference data S. In this embodiment, since the aforementioned number $Q_0$ of difference data S is very large, the second probability density function is estimated assuming that the occurrence frequency distribution of the individual values of the difference data S complies with a Poisson distribution.

Note that it is rational to assume a binomial distribution if the total number $Q_0$ of data points is not very large.

Figure 20:
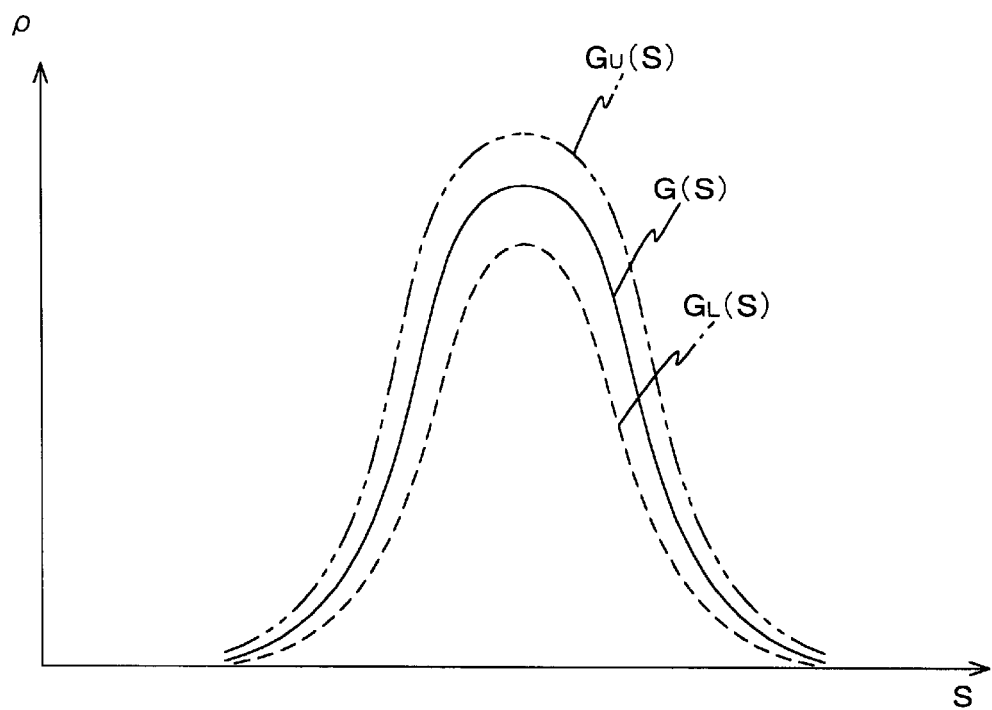
FIG. 20 is a graph showing the confidence interval of the expected occurrence frequencies of difference data.

In step 225, the estimation unit 175 computes the confidence interval of expected occurrence frequencies $G(S)$ of the individual values of the difference data S. Upon computing the confidence interval, the estimation unit 175 computes the confidence interval as an interval of the occurrence frequencies which are not contradictory to the expected occurrence frequency $G(S)$ of each value of the difference data S with a predetermined confidence (e.g., 70%) on the basis of the second probability density function using a known statistical method. FIG. 20 shows upper and lower limit distributions $G_U(S)$ and $G_L(S)$ of the confidence interval computed in this way.

After the confidence interval is obtained, as described above, the estimation unit 175 stores the actual occurrence frequency distribution $H(S)$ and the upper limit distribution $G_U(S)$ of the confidence interval as the distribution of the reference occurrence frequencies in the estimated information storage area 184. Note that the lower limit distribution $G_L(S)$ of the confidence interval is not stored for the following reason. If difference data falls outside the confidence interval to satisfy:

$$G_L(S_L) > H(S_L) \quad (16)$$

pattern defects cannot be determined to be present at any position on the surface of the wafer W, which corresponds to that difference data $S_L$. It merely indicates that pattern defects are highly likely to be present somewhere on the surface of the wafer W.

In step 226, the extraction unit 176 of the difference data classifying unit 172B reads out the actual occurrence frequency distribution $H(S)$ and the upper limit $G_U(S)$ of the confidence interval from the estimated information storage area 184. The unit 176 then checks if each value of the difference data S satisfies "condition 1" given by:

$$G_U(S) < H(S) \quad (17)$$

If NO in step 226, the flow advances to step 227. The extraction unit 176 determines in step 227 that no abnormal difference data candidates are found, sets an abnormal data flag to be "OFF", and ends the subroutine process.

On the other hand, if YES in step 226, the extraction unit 176 extracts the difference data S that satisfies the aforementioned "condition 1" as an abnormal difference data candidate $S_A$, and stores it in the abnormal difference data candidate storage area 185. The flow then advances to step 228.

In step 228, the probability product computation unit 177 of the discrimination unit 172C reads out abnormal difference data candidates $S_A$ from the abnormal difference data candidate storage area 185, and also the actual frequencies $H(S)$ of occurrence and the upper limit $G_U(S)$ of the confidence interval from the estimated information storage area 184. Then, the unit 177 estimates the probability that pattern defects are present at those positions on the surface of the wafer W, which correspond to the abnormal difference data candidates $S_A$, i.e., an abnormal probability $FP(S_A)$ as:

$$FP(S_A) = (H(S_A) - G_U(S_A))/H(S_A) \quad (18)$$

For example, as for a given abnormal difference data candidate $S_A$, if the upper limit $G_U(S_A)$ of the confidence interval is 3.2, and the actual frequency $H(S_A)$ of occurrence is 4, pattern defects are estimated to be present at those positions on the surface of the wafer W, which correspond to four abnormal difference data candidates $S_A$ which account for the actual frequency $H(S_A)$ of occurrence at a probability of 0.2 (=(4−3.2)/4), but they are not present at a probability of 0.8 (=1−0.2).

The probability product computation unit 177 sets abnormal probabilities $FP(S_N)$ of difference data $S_N$ other than the abnormal difference data candidates $S_A$ to be:

$$FP(S_N) = 0 \quad (19)$$

If $(X_{Aj}, Y_{Aj})$ represents the X-Y position in the raw image corresponding to a given abnormal difference data candidate $S_A$ the abnormal difference data candidate $S_A$ and its abnormal probability $FP(S_A)$ are respectively given by:

$$S_A = S_A(X_{Aj}, Y_{Aj}) \qquad (20)$$

$$FP(S_A) = FP[S_A(X_{Aj}, Y_{Aj})] \qquad (21)$$

$$= FP(X_{Aj}, Y_{Aj})$$

In the following description, in order to discriminate the abnormal difference data candidate $S_A$ and abnormal probability $FP(S_A)$ at each position on the surface of the wafer W, they are respectively described by abnormal difference data candidate $S_A(X_{Aj}, Y_{Aj})$ and abnormal probability $FP(X_{Aj}, Y_{Aj})$ In step 229, the probability product computation unit 177 computes abnormal probabilities $FP(X_{Aj}+D, Y_{Aj})$ of corresponding difference data $S(X_{Aj}+D, Y_{Aj})$ of the abnormal difference data candidates $S_A(X_{Aj}, Y_{Aj})$ by equations (18) or (19) above mentioned. In this way, when it is assumed that the abnormal difference data candidate $S_A(X_{Aj}, Y_{Aj})$ is generated due to the presence of pattern defects at the position $(X_{Aj}, Y_{Aj})$ of the raw image, the degree of reflection of pattern defects to the abnormal probability $FP(X_{Aj}+D, Y_{Aj})$ at the position $(X_{Aj}+D, Y_{Aj})$ of the shift image can be quantitatively obtained.

In step 230, the probability product computation unit 177 computes probability products PD by:

$$PD(X_{Aj}, Y_{Aj}) = FP(X_{Aj}, Y_{Aj}) \cdot FP(X_{Aj}+D, Y_{Aj}) \qquad (22)$$

The probability product computation unit 177 then stores the probability products $PD(X_{Aj}, Y_{Aj})$ in the probability product storage area 186.

In step 231, the evaluation unit 178 of the discrimination unit 172C reads out the probability products $PD(X_{Aj}, Y_{Aj})$ from the probability product storage area 186. The unit 178 then checks if each of the probability products $PD(X_{Aj}, Y_{Aj})$ satisfies "condition 2" given by:

$$PD(X_{Aj}, Y_{Aj}) > T \qquad (23)$$

where T is a predetermined threshold value. In this manner, the above assumption that pattern defects are present at the position $(X_{Aj}, Y_{Aj})$ of the raw image can be evaluated. That is, it can be evaluated whether or not the abnormal probability $FP(X_{Aj}, Y_{Aj})$ is relatively large due to the presence of pattern defects at the position $(X_{Aj}, Y_{Aj})$ of the raw image, and whether or not the abnormal probability $FP(X_{Aj}+D, Y_{Aj})$ is relatively large due to the presence of pattern defects at the position $(X_{Aj}+D, Y_{Aj})$ of the shift image. Note that the threshold value T is determined based on design information or experiences.

If NO in step 231, the flow advances to step 232. In step 232, the evaluation unit 178 determines that no abnormal difference data candidates are found, sets an abnormal data flag to be "OFF", and ends the subroutine process.

On the other hand, if YES in step 231, the flow advances to step 233. In step 233, the evaluation unit 178 stores the X-Y position of $PD(X_{Aj}, Y_{Aj})$ that satisfies the aforementioned "condition 2" as an abnormal data position $(X_{Ek}, Y_{Ek})$ (k=1 to the number of data that satisfy "condition 2") in the abnormal data position storage area 187.

In step 234, the evaluation unit 178 sets an abnormal data flag to be "ON", and ends the subroutine process.

Upon completion of the process in the subroutine 205, the flow returns to the main routine.

Referring back to FIG. 16, in step 208 the control unit 179 reads out the abnormal data flag from the abnormal data position storage area 187 as in step 108 in FIG. 4. If the readout abnormal data flag is "ON", the unit 179 also reads out the abnormal data position $(X_{Ek}, Y_{Ek})$, and outputs the inspection result data to the display unit 62, which displays the abnormal data position on the surface of the wafer W.

The operator checks by observing the inspection result displayed on the display unit 62 if pattern defects are actually present at the abnormal data position. Note that the operator inputs control data from the input unit 63 as needed to observe a portion around the defect candidate position via the image pick-up unit 20, and specifies a position on the surface of the wafer W where defects or the like are present. In this manner, inspection of the formation state of repetitive patterns on the wafer W is completed.

In step 209, the controller 55 unloads the wafer W from the sample chamber 22 using the arm 53 in procedures opposite to loading of the wafer W in step 101 above, and stores that wafer W in the cassette 59.

The control unit 179 checks in step 210 if the next wafer to be inspected is present. In this case, YES is determined since only one wafer W has been inspected, and the flow advances to step 211.

In step 211, the next wafer is loaded on the X-Y stage 45 of the image pick-up unit 20 in the same manner as in step 101 described above. After that, steps 202 to 209 are executed to inspect each wafer until NO is determined in step 210. Then, when NO in step 210, and inspection is complete for all the wafers to be inspected, the inspection process ends.

As described above, according to this embodiment, on the basis of a multi-gray level raw image obtained by picking-up the surface of the wafer W, and a shift image obtained by shifting the raw image by the repetition period in the repetition direction of patterns, the distribution of differences between the gray levels of the raw and shift images at identical X-Y positions is statistically analyzed as a probably distribution, thus computing abnormal probabilities of abnormal difference data candidates. Since it is checked based on the computed abnormal probability if each abnormal difference data candidates is abnormal difference data that reflects pattern defects, pattern defects can be accurately found by inspection while completely reflecting multi-gray level information at respective points of the multi-gray level image.

Since the repetition direction and period of the image pick-up result are obtained by analyzing the raw image, those on the surface of the wafer W loaded into the inspection apparatus can be precisely specified, and pattern defects can be accurately found by inspection.

After the abnormal probabilities of abnormal difference data candidates are computed, probability products with abnormal probabilities of difference data that pertain to those positions in the shift image, which correspond to the positions of the abnormal difference data candidates in the raw image are computed, and it is checked based on these probability products if each abnormal difference data candidates is abnormal difference data. Therefore, the positions of pattern defects upon duplicate generation of abnormal relationship data candidates corresponding to pattern defects, which inevitably occurs upon paying attention to the difference between the raw and shift images, can be prevented from being additionally recognized.

Since difference data, the actual occurrence frequency of which is larger than the upper limit value of the confidence interval of the occurrence frequencies, which pertain to the individual difference data values according to a predetermined confidence, is extracted as an abnormal difference data candidate by the statistical scheme, statistically rational abnormal difference data can be extracted.

In the above embodiment, an abnormal data position where pattern defects may be present is obtained using the difference data between the raw and shift image data at identical positions. In place of the difference data between the raw and shift images, ratio data between the raw and shift image data at identical positions may be used. In such case, an abnormal data position where pattern defects may be present can be accurately obtained.

Also, vector data in the first embodiment, i.e., vector data having as components gray levels of at least one shift image data obtained by shifting the raw image by an integer multiple of the repetition period in the pattern repetition direction, and the raw image at identical position, may be used. In such case, an N-dimensional joint probability density function must be estimated in place of the first probability density function in this embodiment.

In the above embodiment, the raw and shift image data are compared. Alternatively, the raw image data may be compared with template image data. In such case, since duplicate generation of abnormal difference data candidates can be prevented, the need for computing probability products in the above embodiment can be obviated, and whether or not each abnormal difference data candidate is abnormal difference data can be accurately evaluated by directly comparing its abnormal probability with a predetermined threshold value. Note that the template image can use a predetermined image such as an image corresponding to patterns to be formed on the substrate in design.

In each of the above embodiments, the environment-controlled scanning electron microscope is used. Alternatively, electron microscopes of other types may be used. Furthermore, an optical microscope may be used.

In each of the above embodiments, wafers are inspected. Alternatively, mask members such as reticles used upon forming patterns on wafers may be inspected. Furthermore, any other objects may be inspected as long as repetitive patterns are formed thereon.

In each of the above embodiments, patterns are repetitively formed one-dimensionally. Alternatively, the present invention can be applied even when patterns are repetitively formed two- or three-dimensionally.

In each of the above embodiments, repetitive patterns formed on the surface of a wafer as the object to be inspected are inspected. The present invention can be applied even to repetitive patterns formed inside the object to be inspected as long as their image can be picked up.

As described in detail above, according to the inspection method of the present invention, pattern defects can be accurately detected by inspection while completely reflecting multi-gray level information at respective points of a multi-gray level image.

Also, according to the inspection apparatus of the present invention, since the formation state of repetitive patterns on the object is inspected using the inspection method of the present invention, pattern defects can be accurately found by inspection.

While the above-described embodiments of the present invention are the presently preferred embodiments thereof, those skilled in the art of lithography system will readily recognize that numerous additions, modifications and substitutions may be made to the above-described embodiments without departing from the spirit and scope thereof. It is intended that all such modifications, additions and substitutions fall within the scope of the present invention, which is best defined by the claims appended below.

What is claimed is:

1. An inspection method for inspecting an object on which a specific pattern is periodically and repetitively formed along a predetermined direction, comprising:

picking-up an image of said object using not less than three gray levels; and obtaining formation information of said specific pattern by statistically analyzing a difference between a raw image obtained as an image pick-up result in said image picking-up, and a reference image, wherein said obtaining the formation information comprises:

obtaining (N−1) shift images obtained by shifting said raw image obtained in said image picking-up by integer multiples of a repetition period in a repetition direction of said specific pattern in the image pick-up result;

defining as data points sets of gray levels at identical positions in N images including said raw image and (N−1) shift images, and plotting data points corresponding to positions in overlapping regions of said N images in an N-dimensional coordinate space; and obtaining pattern formation information of said object based on a state of a distribution of said data points in said N-dimensional coordinate space.

2. The method according to claim 1, wherein said obtaining the shift image comprises:

obtaining said repetition direction and period in said image pick-up result by analyzing said raw image; and obtaining said (N−1) shift images using said obtained repetition direction and period.

3. The method according to claim 1, wherein said obtaining said pattern formation information of the object comprises:

estimating an Nth-order joint probability density function from said distribution of the data points in said N-dimensional coordinate space, and computing a reference occurrence frequency at each coordinate position in said N-dimensional coordinate space using said Nth-order joint probability density function;

computing a relationship between said reference occurrence frequency and an actual occurrence frequency at each coordinate position in said N-dimensional coordinate space; and obtaining said pattern formation information of the object based on said computed relationship.

4. The method according to claim 3, wherein said reference occurrence frequency is an expectation value of a occurrence frequency at each coordinate position in said N-dimensional coordinate space when said Nth-order joint probability density function is used, and said relationship between said reference and actual occurrence frequencies is ratio between said reference and actual occurrence frequencies.

5. The method according to claim 3, wherein said reference occurrence frequency is at least one of upper and lower limit values of a confidence interval according to a predetermined statistical confidence, which pertains to an expectation value of a occurrence frequency at each coordinate position in said N-dimensional coordinate space when said Nth-order joint probability density function is used, and said relationship between said reference and actual occurrence frequencies is difference between said reference and actual occurrence frequencies.

6. The method according to claim 5, wherein
said confidence interval is obtained under an assumption that a occurrence probability at each coordinate position in said N-dimensional coordinate space complies with a binomial distribution which uses said expectation value as an average value.

7. The method according to claim 5, wherein
said confidence interval is obtained under an assumption that a occurrence probability at each coordinate position in said N-dimensional coordinate space complies with a Poisson distribution which uses said expectation value as an average value.

8. The method according to claim 3, wherein
said Nth-order joint probability density function is estimated as a mixture of a plurality of N-dimensional normal distribution type probability density functions.

9. The method according to claim 7, wherein said estimating said Nth-order joint probability density function comprises:
dividing said N-dimensional coordinate space into a plurality of partial spaces by at least one (N−1)-dimensional plane which is perpendicular to a reference line as a set of points having equal coordinate values in said N-dimensional coordinate space;
estimating N-dimensional normal distribution type probability density function of each partial space from the data points in each partial space; and
computing a weighted sum of said N-dimensional normal distribution type probability density functions depending on said corresponding numbers of data points.

10. The method according to claim 9, wherein
said N-dimensional normal distribution type probability density functions corresponding to the plurality of partial spaces are estimated as Nth-order joint probability density functions which have centers on the reference line.

11. The method according to claim 9, wherein
said N-dimensional coordinate space is divided into said plurality of partial spaces to maximize a likelihood of said Nth-order joint probability density function estimated for each of the plurality of partial spaces as a whole.

12. The method according to claim 3, wherein said estimating said Nth-order joint probability density function comprises:
dividing said N-dimensional coordinate space into a plurality of partial spaces by a plurality of (N−1)-dimensional planes which are perpendicular to a reference line as a set of points having equal coordinate values in said N-dimensional coordinate space;
mapping said data points in the plurality of partial spaces onto said (N−1)-dimensional planes perpendicular to said reference line;
computing (N−1)-dimensional normal distribution type probability density functions for said plurality of partial spaces based on said distributions of the mapped data points on said (N−1)-dimensional planes; and
computing a weighted sum of said N-dimensional normal distribution type probability density function of each partial space depending on the corresponding numbers of data points.

13. The method according to claim 12, wherein
said relationship data is one of a difference and ratio between pixels in said raw and reference images.

14. The method according to claim 12, wherein
said specific pattern is formed on a surface of the object.

15. An inspection method for inspecting an object on which a specific pattern is periodically and repetitively formed along a predetermined direction, comprising:
picking-up an image of said object using not less than three gray levels; and
obtaining formation information of said specific pattern by statistically analyzing a difference between a raw image obtained as an image pick-up result in said image picking-up, and a reference image, wherein said obtaining the formation information comprises:
estimating a first probability density function which pertains to occurrence probabilities of relationship data based on a distribution of said relationship data of gray levels in said raw image obtained in said image picking-up and said reference image at identical positions;
estimating a second probability density function that pertains to occurrence frequencies of individual values of the relationship data under an assumption that a probability distribution of the relationship data complies with the first probability density function, and estimating reference occurrence frequencies of the individual values of the relationship data;
extracting abnormal relationship data candidates which are estimated to be abnormal relationship data, which have occurrence frequencies in said distribution of the relationship data that do not comply with said first probability density function at a predetermined confidence, based on said second probability density function, said reference occurrence frequencies, and occurrence frequencies of said individual values of the relationship data in said distribution of the relationship data; and
computing a first probability that each of the abnormal relationship data candidate is the abnormal relationship data.

16. The method according to claim 15, wherein
an upper limit value of a confidence interval corresponding to a predetermined statistic confidence based on the second probability density function is obtained as said reference occurrence frequency, and
the abnormal relationship data candidates are extracted, based on said reference occurrence frequencies and said occurrence frequencies of individual values of the relationship data.

17. The method according to claim 16, wherein
said second probability density function is estimated as one of a binomial distribution type probability density function and a Poisson distribution type probability density function.

18. The method according to claim 15, wherein
said reference image is a predetermined image.

19. The method according to claim 15, wherein
said reference image is a shift image obtained by shifting said raw image by an integer multiple of a repetition period in a repetition direction of said specific pattern in said image pick-up result.

20. The method according to claim 19, further comprising:
computing a product of said first probability and a second probability that relationship data which pertains to a position in the shift image corresponding to the position of said abnormal relationship data candidate in said raw image is said abnormal relationship data; and evaluating based on said probability product appropriateness that said abnormal relationship data candidate is the abnormal relationship data.

21. The method according to claim 19, wherein
said shift image is obtained using said repetition direction and period in said image pick-up result obtained by analyzing said raw image.

22. The method according to claim 15, wherein
said reference image is at least one shift image obtained by shifting said raw image by an integer multiple of a repetition period in a repetition direction of said specific pattern in said image pick-up result, and
said relationship data is vector data having as components gray levels at identical positions in said raw image and said at least one shift image data.

23. The method according to claim 22, wherein
said shift image is obtained using said repetition direction and period in said image pick-up result obtained by analyzing said raw image.

24. The method according to claim 15, wherein
said first probability function is estimated as a normal distribution type probability density function.

25. An inspection apparatus which inspects an object on which a specific pattern is periodically and repetitively formed along a predetermined direction, comprising:
an image pick-up unit which pick up an image of said object using not less than three gray levels; and
a statistical processing unit which obtains formation information of the specific pattern by statistically analyzing a difference between a raw image which is obtained as an image sensing result obtained by using said image pick-up unit, and a reference image, wherein said statistical processing unit comprises:
an image shift unit which obtains (N–1) shift images by shifting said raw image of said image pick-up result obtained by said image pick-up unit by integer multiples of a repetition period in a repetition direction of the specific pattern in the image pick-up result; and
a pattern formation information computation unit which defines data point sets of gray levels at identical positions in N images including the raw image and (N–1) shift images, plotting data points corresponding to positions in overlapping regions of the N images in an N-dimensional coordinate space, and obtaining pattern formation information of the object, based on a distribution of the data points in said N-dimensional coordinate space.

26. The apparatus according to claim 25, wherein said image shift unit comprises:
a repetition information computation unit which obtains said repetition direction and period in said image picking-up result by analyzing said raw image; and
a shift computation unit which obtains said (N–1) shift images using said repetition direction and period obtained by said repetition information computation unit.

27. The apparatus according to claim 25, wherein said pattern formation information computation unit comprises:
a reference frequency arithmetic unit which estimating an Nth-order joint probability density function from said distribution of the data points in said N-dimensional coordinate space, and computing a reference occurrence frequency at each coordinate position in said N-dimensional coordinate space using the Nth-order joint probability density function; and a pattern formation information arithmetic unit which computes a ratio between said reference occurrence frequency and an actual occurrence frequency at each coordinate position in said N-dimensional coordinate space, and obtaining said pattern formation information of the object, based on said computed ratio.

28. The apparatus according to claim 25, wherein
said pattern formation information computation unit obtains confidence information indicating if said specific pattern information is formed on each of formation regions of said specific pattern on said object as said pattern formation information of said object.

29. The apparatus according to claim 28, further comprising:
a defect position arithmetic unit which obtains a candidate position of at least one of foreign matter and a pattern defect on said object, based on said confidence information and positions on said object corresponding to said data points plotted in said N-dimensional coordinate space.

30. An inspection apparatus which inspects an object on which a specific pattern is periodically and repetitively formed along a predetermined direction, comprising:
an image pick-up unit which pick up an image of said object using not less than three gray levels; and
a statistical processing unit which obtains formation information of the specific pattern by statistically analyzing a difference between a raw image which is obtained as an image sensing result obtained by using said image pick-up unit, and a reference image, wherein said statistical processing unit comprises:
an estimation unit which estimates a first probability density function corresponding to occurrence probabilities of relationship data, based on a distribution of said relationship data of gray levels in said raw image obtained as said image pick-up result by said image pick-up unit and said reference image at identical positions, estimates a second probability density function that pertains to occurrence frequencies of said relationship data at individual values of the relationship data under an assumption that a probability distribution of the relationship data complies with said first probability density function, and estimates reference occurrence frequencies of the individual values of said relationship data;
an extraction unit which extracts abnormal relationship data candidates which are estimated to be abnormal relationship data, which have occurrence frequencies in said distribution of said relationship data that do not comply with said first probability density function at a predetermined confidence, based on said estimation results of said estimation unit and occurrence frequencies of said individual values of the relationship data in said distribution of the relationship data; and
an abnormal probability computation unit which computes a first probability that each of the abnormal relationship data candidate is the abnormal relationship data.

31. The apparatus according to claim 30, further comprising:
an image shift computation unit which obtains a shift image by shifting said raw image by an integer multiple of said repetition period in said repetition direction.

32. The apparatus according to claim 31, wherein said image shift unit comprises:
a repetition information computation unit which computes said repetition direction and period in said image pick-up result by analyzing said raw image; and a shift computation unit which obtains said shift image using the repetition direction and period obtained by said repetition information computation unit.

33. The apparatus according to claim 30, wherein said reference image is a shift image obtained by shifting said raw image by an integer multiple of a repetition period in a repetition direction of said specific pattern in said image pick-up result.

34. The apparatus according to claim 33, further comprising:

an image shift computation unit which obtains said shift image by shifting said raw image by an integer multiple of said repetition period in said repetition direction;

a probability product computation unit which computes a probability product of said first probability and a second probability that relationship data corresponding to a position in said shift image corresponding to the position of said abnormal relationship data candidate in said raw image is said abnormal relationship data; and an evaluation unit which evaluates based on said probability product appropriateness that said abnormal relationship data candidate is said abnormal relationship data.

35. The apparatus according to claim 34, wherein said image shift unit comprises:

a repetition information computation unit which computes said repetition direction and period in said image pick-up result by analyzing said raw image; and a shift computation unit which obtains said shift image using said repetition direction and period obtained by said repetition information computation unit.

* * * * *